(12) United States Patent
Vlahov et al.

(10) Patent No.: US 10,188,759 B2
(45) Date of Patent: Jan. 29, 2019

(54) CONJUGATES FOR IMAGING

(71) Applicant: Endocyte, Inc., West Lafayette, IN (US)

(72) Inventors: Iontcho R. Vlahov, West Lafayette, IN (US); Christopher P. Leamon, West Lafayette, IN (US); Hari Krishna R. Santhapuram, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

(21) Appl. No.: 14/989,498

(22) Filed: Jan. 6, 2016

(65) Prior Publication Data
US 2016/0193371 A1 Jul. 7, 2016

Related U.S. Application Data

(60) Provisional application No. 62/100,677, filed on Jan. 7, 2015.

(51) Int. Cl.
A61K 51/04 (2006.01)
A61K 51/08 (2006.01)

(52) U.S. Cl.
CPC ............................... A61K 51/0459 (2013.01)

(58) Field of Classification Search
CPC .................................................. A61K 51/0459
See application file for complete search history.

(56) References Cited

U.S. PATENT DOCUMENTS

| | | | |
|---|---|---|---|
| 4,691,024 A | 9/1987 | Kunikatsu et al. |
| 4,713,249 A | 12/1987 | Schroder |
| 5,103,018 A | 4/1992 | Motomichi et al. |
| 5,266,333 A | 11/1993 | Cady et al. |
| 5,418,982 A | 5/1995 | Kishi |
| 5,627,165 A | 5/1997 | Glazier |
| 5,795,877 A | 8/1998 | Jackson et al. |
| 5,863,536 A | 1/1999 | Jackson et al. |
| 5,866,679 A | 2/1999 | DeFeo-Jones et al. |
| 5,902,817 A | 5/1999 | Jackson et al. |
| 5,948,750 A | 9/1999 | Garsky et al. |
| 5,962,237 A | 10/1999 | Ts'o et al. |
| 5,962,521 A | 10/1999 | Jackson et al. |
| 5,968,915 A | 10/1999 | Jackson et al. |
| 5,998,362 A | 12/1999 | Feng et al. |
| 6,054,444 A | 4/2000 | Jackson et al. |
| 6,127,333 A | 10/2000 | Brady et al. |
| 6,174,858 B1 | 1/2001 | Brady et al. |
| 6,177,404 B1 | 1/2001 | DeFeo-Jones et al. |
| 6,232,287 B1 | 5/2001 | Ruoslahti et al. |
| 6,368,598 B1 | 4/2002 | D'Amico et al. |
| 6,391,305 B1 | 5/2002 | Feng et al. |
| 6,428,785 B1 | 8/2002 | Gocken |
| 6,479,470 B1 | 11/2002 | Kozikowski et al. |
| 6,528,499 B1 | 3/2003 | Kozikowski et al. |
| 6,875,886 B2 | 4/2005 | Frangioni |
| 6,946,133 B1 | 9/2005 | Schlom et al. |
| 7,008,765 B1 | 3/2006 | Bussemakers et al. |
| 7,128,893 B2 | 10/2006 | Leamon et al. |
| 7,129,254 B2 | 10/2006 | Berger et al. |
| 7,147,837 B2 | 12/2006 | Lauffer et al. |
| 7,192,586 B2 | 3/2007 | Bander |
| 7,232,805 B2 | 6/2007 | Weinshenker et al. |
| 7,361,338 B2 | 4/2008 | Jakobovits et al. |
| 7,381,745 B2 | 6/2008 | Kozikowski et al. |
| 7,408,079 B2 | 8/2008 | Pomper et al. |
| 7,485,299 B2 | 2/2009 | Afar et al. |
| 7,514,078 B2 | 4/2009 | Bander et al. |
| 7,534,580 B2 | 5/2009 | Reeves et al. |
| 7,601,332 B2 | 10/2009 | Vlahov et al. |
| 7,635,682 B2 | 12/2009 | Denmeade et al. |
| 7,638,122 B2 | 12/2009 | Yu et al. |
| 7,659,395 B2 | 2/2010 | Pajouhesh et al. |
| 7,662,795 B2 | 2/2010 | Rodriguez et al. |
| 7,696,185 B2 | 4/2010 | Berkman |
| 7,713,944 B2 | 5/2010 | Kinberger et al. |
| 7,740,847 B2 | 6/2010 | Allan et al. |
| 7,767,202 B2 | 8/2010 | Pardoll et al. |
| 7,767,803 B2 | 8/2010 | Diener et al. |
| 7,794,929 B2 | 9/2010 | Baylin et al. |
| 7,872,235 B2 | 1/2011 | Rousso et al. |
| 7,875,586 B2 | 1/2011 | Kovbasnjuk et al. |
| 7,879,981 B2 | 2/2011 | Obata |
| RE42,275 E | 4/2011 | Berkman |

(Continued)

FOREIGN PATENT DOCUMENTS

| | | |
|---|---|---|
| CA | 2606138 | 10/2005 |
| EP | 0116208 | 8/1984 |

(Continued)

OTHER PUBLICATIONS

Wang et al., Synthesis, Purification, and Tumor Cell Uptake of 67Ga-Deferoxamine-Folate, a Potential Radiopharmaceutical for Tumor Imaging, Bioconjugate Chemistry (1996), 7(1), 56-62.*
Baur et al., Synthesis and labelling of Df-DUPA-Pep with gallium-68 and zirconium-89 as new PSMA ligandsJournal of Radioanalytical and Nuclear Chemistry (2014), 299(3), 1715-1721.*
Vosjan et al., nature protocols, vol. 5 No. 4, 2010, pp. 739-743.*
Banerjee, S. et al., "Sequential SPECT and Optical Imaging of Experimental Models of Prostate Cancer with a Dual Modality Inhibitor of the Prostate-Specific Membrane Antigen," Angewandte Chemie International Edition, 2011, 50, 9167-9170.
Banerjee, S.R. et al. "Synthesis and Evaluation of Technetium-99m- and Rhenium-Labeled Inhibitors of the Prostate-Specific Membrane Antigen (PSMA)," J Med Chem. Aug. 14, 2008; 51(15): 4504-4517.

(Continued)

Primary Examiner — Sudhakar Katakam
(74) Attorney, Agent, or Firm — Barnes & Thornburg LLP

(57) ABSTRACT

The invention described herein relates to conjugates and compositions for imaging, diagnosing, and/or monitoring diseases using radionuclide-based imaging. In particular, the invention described herein relates to conjugates and compositions for imaging, diagnosing, and/or monitoring diseases using positron emission tomography.

7 Claims, No Drawings

(56) References Cited

U.S. PATENT DOCUMENTS

| | | |
|---|---|---|
| 7,990,533 B2 | 8/2011 | Maier et al. |
| 8,000,773 B2 | 8/2011 | Rousso et al. |
| 8,101,369 B2 | 1/2012 | Nam et al. |
| 8,101,713 B2 | 1/2012 | Cuello et al. |
| 8,105,568 B2 | 1/2012 | Vlahov et al. |
| 8,153,595 B2 | 4/2012 | Chen |
| 8,211,402 B2 | 7/2012 | Babich et al. |
| 8,211,473 B2 | 7/2012 | Troiano et al. |
| 8,211,635 B2 | 7/2012 | Barton |
| 8,258,111 B2 | 9/2012 | Shen et al. |
| 8,404,817 B2 | 3/2013 | Sherman et al. |
| 8,414,898 B2 | 4/2013 | Afar et al. |
| 8,445,851 B2 | 5/2013 | Rousso et al. |
| 8,450,290 B2 | 5/2013 | Worm et al. |
| 8,465,725 B2 | 6/2013 | Babich et al. |
| 8,507,434 B2 | 8/2013 | Popel et al. |
| 8,557,772 B2 | 10/2013 | Popel et al. |
| 8,606,349 B2 | 12/2013 | Rousso et al. |
| 8,644,910 B2 | 2/2014 | Rousso et al. |
| 8,685,891 B2 | 4/2014 | Muraca |
| 8,703,918 B2 | 4/2014 | Colombatti et al. |
| 8,772,226 B2 | 6/2014 | Denmeade et al. |
| 8,772,459 B2 | 6/2014 | Ho et al. |
| 8,816,095 B2 | 8/2014 | Brown et al. |
| 8,852,630 B2 | 10/2014 | Spiegel et al. |
| 8,859,509 B2 | 10/2014 | Spiegel et al. |
| 8,877,970 B2 | 11/2014 | Zimmerman et al. |
| 8,940,871 B2 | 1/2015 | Wu et al. |
| 8,946,388 B2 | 2/2015 | Sahin et al. |
| 8,987,319 B2 | 3/2015 | Miller |
| 9,044,468 B2 | 6/2015 | Pomper et al. |
| 9,242,012 B2 | 1/2016 | Ma et al. |
| 9,278,067 B2 | 3/2016 | Boulikas |
| 9,636,413 B2 | 5/2017 | Vlahov et al. |
| 2001/0031252 A1 | 10/2001 | Low et al. |
| 2002/0001782 A1 | 1/2002 | Watanabe et al. |
| 2002/0055121 A1 | 5/2002 | Vielkind |
| 2002/0103136 A1 | 8/2002 | Feng |
| 2002/0115596 A1 | 8/2002 | Garsky et al. |
| 2002/0132983 A1 | 9/2002 | Junghans |
| 2003/0035804 A1 | 2/2003 | D'Amico et al. |
| 2003/0086900 A1 | 5/2003 | Low et al. |
| 2003/0133927 A1 | 7/2003 | DeFeo-Jones et al. |
| 2003/0138432 A1 | 7/2003 | Glazier |
| 2003/0207808 A1 | 11/2003 | Savitzky et al. |
| 2003/0215456 A1 | 11/2003 | Yao et al. |
| 2003/0220241 A1 | 11/2003 | DeFeo-Jones et al. |
| 2003/0232760 A1 | 12/2003 | Garsky et al. |
| 2004/0001846 A1 | 1/2004 | Israeli et al. |
| 2004/0002478 A1 | 1/2004 | Kozikowski et al. |
| 2004/0018203 A1 | 1/2004 | Pastan et al. |
| 2004/0029778 A1 | 2/2004 | Isaacs |
| 2004/0033195 A1 | 2/2004 | Leamon et al. |
| 2004/0052727 A1 | 3/2004 | Dalton et al. |
| 2004/0054190 A1 | 3/2004 | Pomper et al. |
| 2004/0058857 A1 | 3/2004 | Yao |
| 2004/0110723 A1 | 6/2004 | Frangioni |
| 2004/0146516 A1 | 7/2004 | Roben et al. |
| 2004/0213791 A1 | 10/2004 | Bander et al. |
| 2004/0242582 A1 | 12/2004 | Green et al. |
| 2005/0002942 A1 | 1/2005 | Vlahov et al. |
| 2005/0107325 A1 | 5/2005 | Manoharan et al. |
| 2005/0119166 A1 | 6/2005 | Brady et al. |
| 2005/0158780 A1 | 7/2005 | Lupold et al. |
| 2005/0234247 A1 | 10/2005 | Klar et al. |
| 2005/0239138 A1 | 10/2005 | Hess et al. |
| 2005/0239739 A1 | 10/2005 | Matulic-Adamic |
| 2005/0245486 A1 | 11/2005 | Frangioni |
| 2006/0024317 A1 | 2/2006 | Boyd et al. |
| 2006/0052312 A1 | 3/2006 | Erhardt et al. |
| 2006/0062793 A1 | 3/2006 | Webb et al. |
| 2006/0105975 A1 | 5/2006 | Pendergrast et al. |
| 2006/0106047 A1 | 5/2006 | Jiang et al. |
| 2006/0140871 A1 | 6/2006 | Sillerud |
| 2006/0148718 A1 | 7/2006 | Brady et al. |
| 2006/0155021 A1 | 7/2006 | Lenges et al. |
| 2006/0155146 A1 | 7/2006 | Lenges et al. |
| 2007/0010014 A1 | 1/2007 | Wood et al. |
| 2007/0020327 A1 | 1/2007 | Fikes et al. |
| 2007/0031326 A1 | 2/2007 | Shirvan et al. |
| 2007/0031438 A1 | 2/2007 | Junghans |
| 2007/0041901 A1 | 2/2007 | Diener et al. |
| 2007/0117153 A1 | 5/2007 | Bieniarz et al. |
| 2007/0128670 A1 | 6/2007 | Klatzmann et al. |
| 2007/0134332 A1 | 6/2007 | Turnell et al. |
| 2007/0142296 A1 | 6/2007 | McBride et al. |
| 2007/0148662 A1 | 6/2007 | Israeli et al. |
| 2007/0160617 A1 | 7/2007 | Ma et al. |
| 2007/0172422 A1 | 7/2007 | Glazier |
| 2007/0179100 A1 | 8/2007 | Manoharan |
| 2007/0219165 A1 | 9/2007 | Berkman et al. |
| 2007/0225213 A1 | 9/2007 | Kosak |
| 2007/0244055 A1 | 10/2007 | Brady et al. |
| 2007/0254316 A1 | 11/2007 | Rodriguez et al. |
| 2007/0254317 A1 | 11/2007 | Busseret-Michel et al. |
| 2008/0008719 A1 | 1/2008 | Bowdish et al. |
| 2008/0089869 A1 | 4/2008 | Denmeade et al. |
| 2008/0114153 A1 | 5/2008 | Steeves et al. |
| 2008/0175789 A1 | 7/2008 | Frangioni |
| 2008/0176821 A1 | 7/2008 | Kozikowski et al. |
| 2008/0193381 A1 | 8/2008 | Babich et al. |
| 2008/0214436 A1 | 9/2008 | Yu et al. |
| 2008/0248052 A1 | 10/2008 | Vlahov et al. |
| 2008/0269105 A1 | 10/2008 | Taft et al. |
| 2008/0311037 A1 | 12/2008 | Heston et al. |
| 2009/0117042 A1 | 5/2009 | Pomper et al. |
| 2009/0123467 A1 | 5/2009 | Bedi et al. |
| 2009/0180951 A1 | 7/2009 | Zimmerman et al. |
| 2009/0247614 A1 | 10/2009 | Manoharan et al. |
| 2009/0258002 A1 | 10/2009 | Barrett et al. |
| 2009/0274625 A1 | 11/2009 | Denmeade et al. |
| 2010/0048490 A1 | 2/2010 | Vlahov et al. |
| 2010/0092496 A1 | 4/2010 | Boyd et al. |
| 2010/0178246 A1 | 7/2010 | Babich et al. |
| 2010/0183509 A1 | 7/2010 | Babich et al. |
| 2010/0183517 A1 | 7/2010 | Berkman |
| 2010/0209343 A1 | 8/2010 | Bander et al. |
| 2010/0240701 A1 | 9/2010 | Vlahov et al. |
| 2011/0008253 A1 | 1/2011 | Babich et al. |
| 2011/0027180 A1 | 2/2011 | Magnani |
| 2011/0027274 A1 | 2/2011 | Cheng et al. |
| 2011/0064657 A1 | 3/2011 | Pomper et al. |
| 2011/0142760 A1 | 6/2011 | Pomper et al. |
| 2011/0176998 A1 | 7/2011 | Pomper et al. |
| 2011/0200677 A1 | 8/2011 | Chandran et al. |
| 2011/0288152 A1 | 11/2011 | Low et al. |
| 2012/0009121 A1 | 1/2012 | Pomper et al. |
| 2012/0276162 A1 | 11/2012 | Zale et al. |
| 2012/0322741 A1* | 12/2012 | Low .................. A61K 49/0032 514/19.5 |
| 2014/0107316 A1 | 4/2014 | Vlahov et al. |
| 2014/0140925 A1 | 5/2014 | Leamon et al. |
| 2015/0110814 A1* | 4/2015 | Olson ................. A61K 31/4166 424/178.1 |
| 2016/0067341 A1 | 3/2016 | Low et al. |
| 2016/0151508 A1 | 6/2016 | Low et al. |
| 2016/0361376 A1 | 12/2016 | Vlahov et al. |
| 2016/0361432 A1 | 12/2016 | Vlahov et al. |
| 2016/0361433 A1 | 12/2016 | Vlahov et al. |

FOREIGN PATENT DOCUMENTS

| | | |
|---|---|---|
| JP | 2002-506204 | 2/2002 |
| JP | 2004-536034 | 12/2004 |
| JP | 2005-274569 | 10/2005 |
| JP | 2006-501149 | 1/2006 |
| JP | 2007-521803 | 8/2007 |
| WO | WO 88/01622 | 3/1988 |
| WO | WO 99/45374 | 9/1999 |
| WO | WO 2002/062398 | 8/2002 |
| WO | WO 2002/098885 | 12/2002 |
| WO | WO 2003/060523 | 7/2003 |
| WO | WO 2003/092742 | 11/2003 |
| WO | WO 2003/097647 | 11/2003 |

(56) References Cited

FOREIGN PATENT DOCUMENTS

| | | |
|---|---|---|
| WO | WO 2004/010957 | 2/2004 |
| WO | WO 2004/069159 | 8/2004 |
| WO | WO 2005/082023 | 9/2005 |
| WO | WO 2006/012527 | 2/2006 |
| WO | WO 2006/093991 | 9/2006 |
| WO | WO 2006/096754 | 9/2006 |
| WO | WO 2006/136564 | 12/2006 |
| WO | WO 2007/022494 | 2/2007 |
| WO | WO 2007/106869 | 9/2007 |
| WO | WO 2008/057437 | 5/2008 |
| WO | WO 2008/058192 | 5/2008 |
| WO | WO 2008/121949 | 10/2008 |
| WO | WO 2009/026177 | 2/2009 |
| WO | WO 2009/082606 | 2/2009 |
| WO | WO 2009/002993 | 12/2009 |
| WO | WO 2010/014933 | 2/2010 |
| WO | WO 2010/065902 | 6/2010 |
| WO | WO 2011/106639 | 9/2011 |
| WO | WO 2014/078484 | 5/2014 |
| WO | WO 2014/134543 | 9/2014 |

OTHER PUBLICATIONS

Bennett, V.J.," Analysis of fluorescently labeled substance P analogs: binding, imaging and receptor activation," BMC Chemical Biology, 2001, 1:1. doi:10.1186/1472-6769-1-1.
Chen, Ying, et al., "Radiohalogenated Prostate-Specific Membrane Antigen (PSMA)-Based Ureas as Imaging Agents for Prostate Cancer," J. Med. Chem., 2008, 51 (24), pp. 7933-7943.
Cole et al., "Cancer theranostics: the rise of targeted magnetic nanoparticles," Trends in Biotechnology, 2011, 29, 323-332.
Davis, Mindy I., et al., "Crystal Structure of Prostate-Specific Membrane Antigen, A Tumor Marker and Peptidase", Apr. 26, 2005, PNAS, vol. 102, No. 17, pp. 5981-5986.
Definition of ligand, Random House Kernerman Webster's College Dictionary, downloaded on Jan. 25, 2014 from http://www.thefreedictionary.com/ligand, 1 page.
Eder et al., 68Ga-complex lipophilicity and the targeting property of a urea-based PSMA inhibitor for PET imaging, Bioconjugate Chemistry, 2012; 23:688-697.
Farokhzad, et al., "Nanoparticle-Aptamer Bioconjugates: A New Approach for Targeting Prostate Cancer Cells," Cancer Research 64, pp. 7668-7672 (2004).
Foss, Catherine A., et al, "Radiclabeled small-molecule ligands for prostate-specific membrane antigen: in vivo imaging in experimental models of prostate cancer." Clinical cancer research 11.11 (2005): 4022-4028.
Gomez-Hens et al., "Long wavelength fluorophores: new trends in their analytical use," Trends in Analytical Chemistry, 2004; 23:127-136.
Henne, et al., "Synthesis and activity of a folate peptide camptothecin prodrug," ScienceDirect, Bioorganic & Medical Chemistry Letters 16 (2006) 5350-5355.
Hillier, Shawn M., et al., "Preclinical Evaluation of Novel Glutamate-Urea-Lysine Analogues That Target Prostate-Specific Membrane Antigen as Molecular Imaging Pharmaceuticals for Prostate Cancer," Cancer Res. Sep. 1, 2009;69(17):6932-40.
Jackson, Paul F., et al., "Design of NAALADase Inhibitors: A Novel Neuroprotective Strategy", 2001, Current Medicinal Chemistry, vol. 8, No. 8, pp. 949-957.
Jayaprakash, Sarva, et al. "Design and synthesis of a PSMA inhibitor—doxorubicin conjugate for targeted prostate cancer therapy." ChemMedChem 1.3 (2006): 299-302.
Kaur, G. et al., "Biological evaluation of tubulysin A: a potential anticancer and antiangiogenic natural product," Biochem. J., 2006, 396, 235-242.
Kozikowski, Alan P., et al., "Design of Remarkably Simple, Yet Potent Urea-Based Inhibitors of Glutamate Carbozypeptidase II (NAALADase)"2, 001, Journal of Medicinal Chemistry, vol., 44, No. 3, pp. 298-301.

Kozikowski, Alan P., et al., "Synthesis of Urea-Based Inhibitors as Active Site Probes of Glutamate Carboxypeptodase II: Efficacy as Analgesic Agents", 2004, Journal of Medicinal Chemistry, vol., 47, No. 7, pp. 1729-1738.
Kularatne et al., "Prostate-specific membrane antigen targeted imaging and therapy of prostate cancer using a PSMA inhibitor as a homing ligand," Molecular Pharmaceutics, 6(3): 780-789 (2009).
Kularatne, S., "Synthesis and Biological Analysis of Prostate-Specific Membrane Antigen-Targeted Anticancer Prodrugs," J. Med. Chem, 2010, 53(21), 7767-7777.
Larock, "Comprehensive Organic Transformations, a guide to functional group preparations," VCH Publishers, Inc. New York (1989).
Lu, G. et al., "Synthesis and SAR of $^{99m}$Tc/Re-labeled small molecule prostate specific membrane antigen inhibitors with novel polar chelates," Bioorganic and Medicinal Chemistry Letters, 2013, 23, 1557-1563.
Lupold, et al., "Identification and characterization of nuclease-stabilized RNA molecules that bind human prostate cancer cells via the prostate-specific membrane antigen." Cancer Res. 2002; 62:4029-4033.
Majer, Pavel., et al., "Synthesis and Biological Evaluation of Thiol-Based Inhibitors of Glutamate Carboxypeptodase II: Discovery of an Orally Active GCP II Inhibitor", 2003, Journal of Medicinal Chemistry, vol., 46, No. 10, pp. 1989-1996.
Maresca, K. P., "A Series of Halogenated Heterodimeric Inhibitors of Prostate Specific Membrane Antigen (PSMA) as Radiolabeled Probes for Targeting Prostate Cancer," J. Med. Chem., 2009, 52 (2), pp. 347-357.
Maresca, K., et al., "Molecular targeting of prostate cancer with small molecule inhibitors of prostate specific membrane antigen (PSMA)," J. Nucl. Med. 2007, 48 (Supplement 2):25P.
Martin, et al., Helv. Chim. Acta, 78, 486-504 (1995) and Abstract.
McNamara et al, Cell type specific delivery of siRNAs with aptamer-siRNA chimeras, Nature Biotechnolgy, 2006; 24: 1005-1015.
Melby, et at., Cancer Research 53(8), pp. 1755-1760 (1993).
Mesters, et al., et al., "Structure of Glutamate Carboxypeptidase II, a Drug Target in Neuronal Damage and Prostate Cancer"2, 006, The EMBO Journal, vol. 25, No. 6, pp. 1375-1384.
Olsnes, S., et al., Immunology Today, 10, pp. 291-295 (1989).
Paranjpe, et al., "Tumor-targeted bioconjugate based delivery of camptothecin: design, synthesis and in vitro evaluation," ScienceDirect Journal of Controlled Release 100 (2004) 275-292.
Pathalk et al., Enzymic protecting group techniques in organic synthesis, Stereosel. Biocatal. 775-797 (2000).
Peltier et al., "The Total Synthesis of Tubulysin D," J. Am. Chem. Soc. 128:16018-19 (2006).
Pubchem, Compound summary for: CID 58099954, Aug. 19, 2012.
Radioisotopes in Medicine, from http://www.word-nuclear.org/information-library/non-power-nuclear applications/radioisotopes-research/radioisotopes-in-medicine.aspx, Dec. 28, 2016, pp. 1-20.
Ranasinghe, M. G., et al., "Facile Synthesis of Unsymmetrical Thiolsulfonates via Sulfonylation of Mercaptans", 1988, Synthetic Communications, vol. 18, No. 3, pp. 227-232.
Reddy et al., "PSMA-specific anti-tumor activity of the targeted-tubulysin conjugate, EC1169," American Association for Cancer Research Annual Meeting(Apr. 8, 2013) Poster.
Reddy et al., "PSMA-specific anti-tumor activity of the targeted-tubulysin conjugate, EC1169," American Association for Cancer Research Annual Meeting(Apr. 8, 2013) Presentation Abstract.
Roy, et al., "DUPA Conjugation of a Cytotoxic Indenoisoquinoline Topoisomerase I Inhibitor for Selective Prostate Cancer Cell Targeting," J. Med. Chem. 58 (2015) 3094-3103.
Theodora E. Greene & Peter G.M. Wuts, "Protective Groups ion Organic Synthesis," 2d edition, John Wiley & Sons, Inc. New York (1991).
Truffert, et al., Tetrahedron, 52:3005 (1996).
Vlahov, et al., "Design and regioselective synthesis of a new generation of targeted chemotherapeutics. Part 1: EC145, a folic acid conjugate of desacetylvinblastine monohydrazide," ScienceDirect, Bioorganic & Medical Chemistry Letters 16 (2006) 5093-5096.

(56) References Cited

OTHER PUBLICATIONS

Wang et al., "Prostate-Specific Membrane Antigen Targeted Tubulysin Conjugates for Cancer Therapy," *246th ACS National Meeting and Exposition*(Sep. 8, 2013) Poster.
Yang, et al., "Characterization of the pH of Folate Receptor-Containing Endosomes and the Rate of Hydrolysis of Internalized Acid-Labile Folate-Drug Conjugates," JPET 321: 462-468, 2007.

* cited by examiner

CONJUGATES FOR IMAGING

CROSS-REFERENCE TO RELATED APPLICATIONS

This application claims the benefit of priority under 35 U.S.C. § 119(e) to U.S. Provisional Patent Application Ser. No. 62/100,677, filed Jan. 7, 2015, the entirety of which is hereby expressly incorporated by reference.

TECHNICAL FIELD

The invention described herein relates to conjugates and compositions for imaging, diagnosing, and/or monitoring diseases using radionuclide-based imaging. In particular, the invention described herein relates to conjugates and compositions for imaging, diagnosing, and/or monitoring diseases using positron emission tomography.

BACKGROUND

Positron emission tomography (PET) is a nuclear imaging methodology that detects pairs of gamma rays emitted indirectly by a positron-producing radionuclide. Because the two emitted gamma rays travel in exactly opposite directions, it is possible to locate their site of origin and thereby reconstruct a three-dimensional image of all positron emitters from a computer analysis of the origins of emitted gamma rays.

Vitamin receptors are overexpressed on certain cells, including many cancer cell types, activated macrophages, and activated monocytes. In particular, folate receptors are overexpressed on many cancers. The folate receptor, a 38 KD GPI-anchored protein that binds the vitamin folic acid with high affinity (<1 nM), is overexpressed on many malignant tissues, including ovarian, breast, bronchial, and brain cancers. It is estimated that 95% of all ovarian carcinomas overexpress the folate receptor. In contrast, with the exception of kidney, choroid plexus, and placenta, normal tissues express low or non-detectable levels of the folate receptor. Most cells also use an unrelated reduced folate carrier to acquire the necessary folic acid.

Following receptor binding of vitamins to vitamin receptors, such as folic acid and analogs and derivatives of folic acid to folate receptors, rapid endocytosis delivers the vitamin into the cell, where it is unloaded in an endosomal compartment at lower pH. Importantly, covalent conjugation of small molecules, proteins, and even liposomes to vitamins and other vitamin receptor binding ligands does not block the ability of the ligand to bind to its receptor, and therefore, such conjugates can readily be delivered to and can enter cells by receptor-mediated endocytosis. Accordingly, imaging agents can be targeted to vitamin receptors, including the folate receptor, for delivery into vitamin receptor expressing cells.

The prostate is a male reproductive organ that functions to produce and store seminal fluid, which provides nutrients and fluids for the survival of sperm introduced into the vagina during reproduction. Like other tissues, the prostate gland may develop either malignant (cancerous) or benign (non-cancerous) tumors. Prostate cancer is reportedly one of the most common male cancers in western societies, and is the second leading form of malignancy among American men.

Prostate-specific membrane antigen (PSMA) is a biomarker that is overexpressed on prostate cancer cells. PSMA is over-expressed in malignant prostate tissues when compared to other organs in the human body such as kidney, proximal small intestine, and salivary glands. PSMA is also expressed on the neovasculature within many non-prostate solid tumors, including lung, colon, breast, renal, liver and pancreatic carcinomas, but not on normal vasculature. PSMA is a type II cell surface membrane-bound glycoprotein with ~110 kD molecular weight, including an intracellular segment (amino acids 1-18), a transmembrane domain (amino acids 19-43), and an extensive extracellular domain (amino acids 44-750). Though the functions of the intracellular segment and the transmembrane domains are currently reported to be insignificant, the extracellular domain is involved in several distinct activities. For example, PSMA plays a role in the central nervous system, where it metabolizes N-acetyl-aspartyl glutamate (NAAG) into glutamic and N-acetyl aspartic acid. PSMA also plays a role in the proximal small intestine where it removes γ-linked glutamate from poly-γ-glutamated folate and α-linked glutamate from peptides and small molecules.

Though the particular function of PSMA on prostate cancer cells remains unresolved, PSMA is known to undergo rapid internalization into the cell, similar to cell surface bound receptors like vitamin receptors. PSMA is internalized through clathrin-coated pits and subsequently can either recycle to the cell surface or enter lysosomes. Accordingly, imaging agents can be targeted to PSMA for delivery into PSMA expressing cells, such as prostate cancer cells.

SUMMARY

It has been discovered herein that the conjugates and compositions described herein, comprising folate or a PSMA ligand, are useful for targeting and delivering radionuclides for diagnosing, imaging, and/or monitoring various diseases using PET imaging.

Several illustrative embodiments are described by the following clauses:

1. A conjugate of the formula

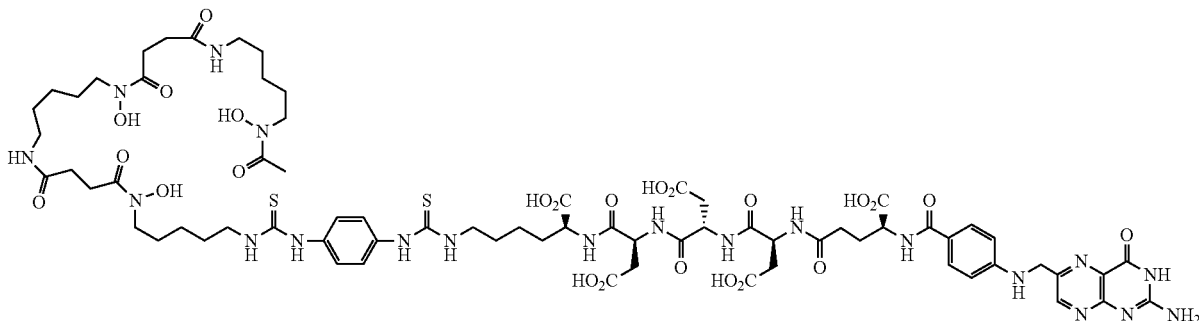 [SMILES: CC(=O)N(O)CCCCCNC(=O)CCC(=O)N(O)CCCCCNC(=O)CCC(=O)N(O)CCCCCNC(=S)Nc1ccc(NC(=S)NCCCC[C@H](NC(=O)[C@H](CC(=O)O)NC(=O)[C@H](CC(=O)O)NC(=O)[C@H](CC(=O)O)NC(=O)CC[C@H](NC(=O)c2ccc(NCc3cnc4nc(N)[nH]c(=O)c4n3)cc2)C(=O)O)C(=O)O)cc1]

or a pharmaceutically acceptable salt thereof.

2. A conjugate of the formula
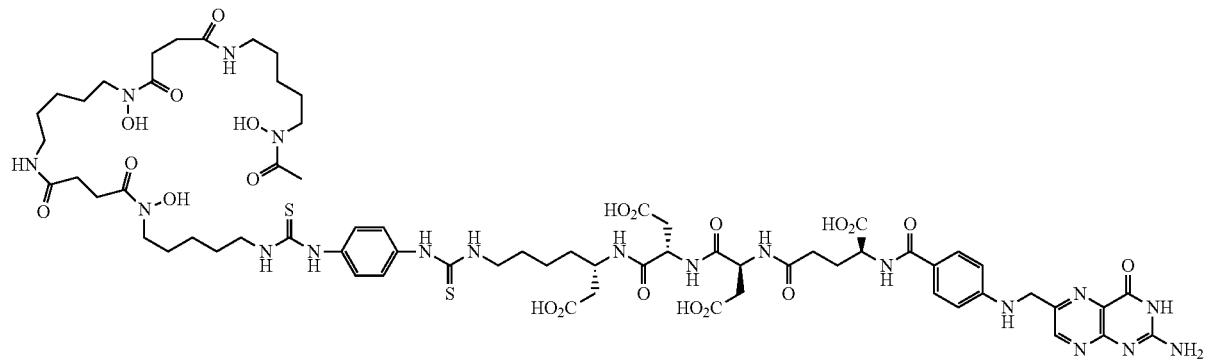 [SMILES: CC(=O)N(O)CCCCCNC(=O)CCC(=O)N(O)CCCCCNC(=O)CCC(=O)N(O)CCCCCNC(=S)Nc1ccc(NC(=S)NCCCC[C@@H](CC(=O)O)NC(=O)[C@H](CC(=O)O)NC(=O)[C@H](CC(=O)O)NC(=O)CC[C@H](NC(=O)c2ccc(NCc3cnc4nc(N)[nH]c(=O)c4n3)cc2)C(=O)O)cc1]
or a pharmaceutically acceptable salt thereof.
3. A conjugate of the formula
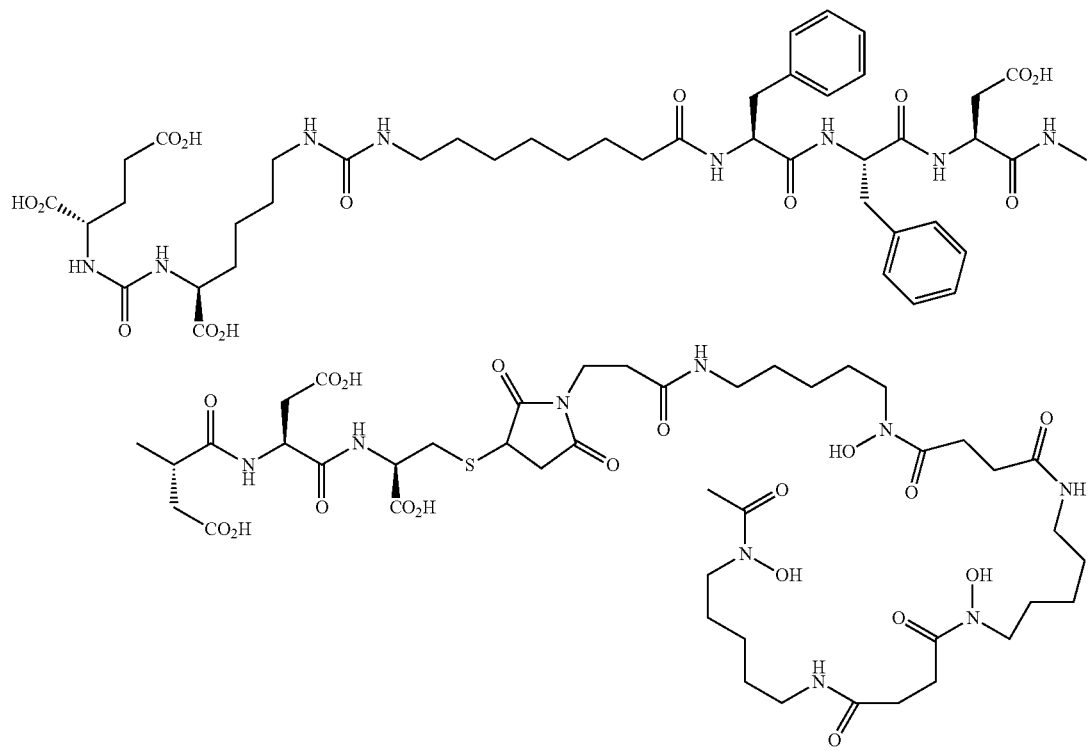
or a pharmaceutically acceptable salt thereof.
4. A conjugate of the formula
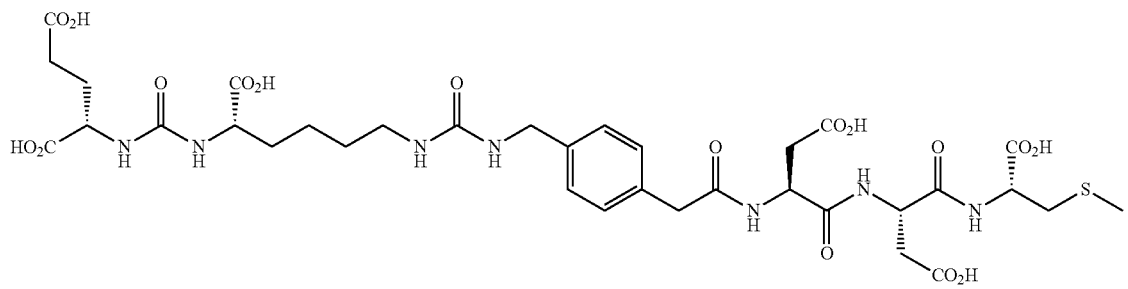

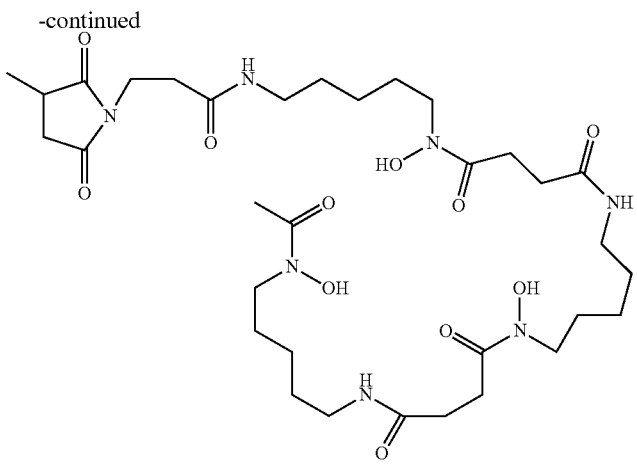

or a pharmaceutically acceptable salt thereof.

5. A conjugate of the formula

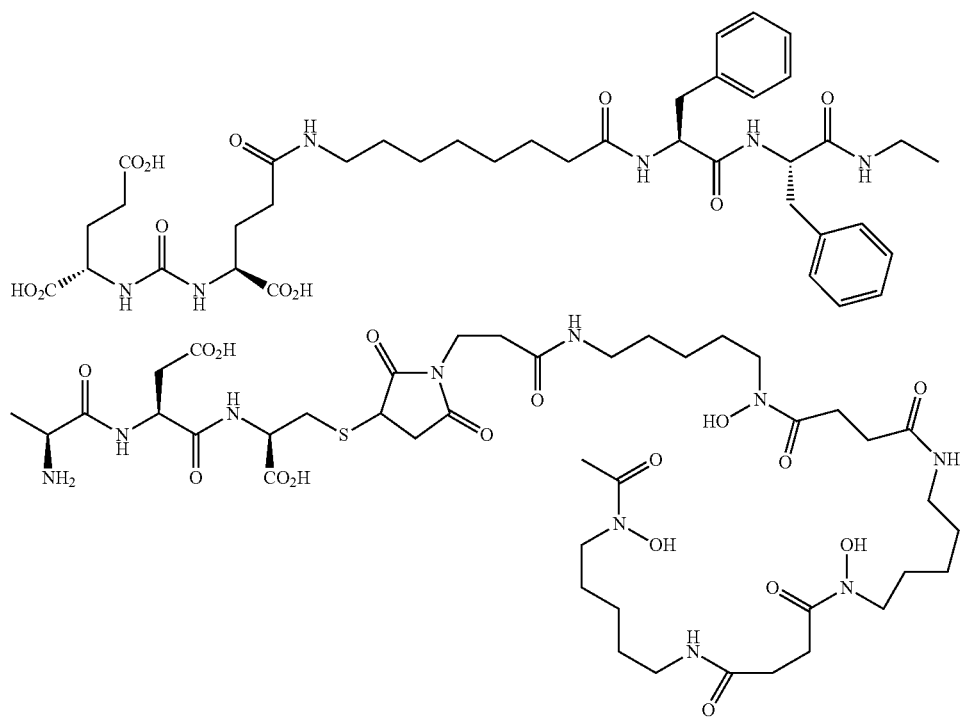

or a pharmaceutically acceptable salt thereof.

6. The conjugate, or pharmaceutically acceptable salt thereof, of any of the preceding clauses wherein the conjugate, or pharmaceutically acceptable salt thereof, is complexed with a radionuclide.

7. The conjugate, or pharmaceutically acceptable salt thereof, of clause 6 wherein the radionuclide is a positron emitting radionuclide.

8. The conjugate, or pharmaceutically acceptable salt thereof, of clause 6 or 7 wherein the radionuclide is a metal ion.

9. The conjugate, or pharmaceutically acceptable salt thereof, of clause 8 wherein the metal ion is selected from the group consisting of $^{89}$Zr, $^{45}$Ti, $^{51}$Mn, $^{64}$Cu, $^{62}$Cu, $^{61}$Cn, $^{60}$Cu, $^{63}$Zn, $^{82}$Rb, $^{86}$Y, $^{68}$Ga, and $^{66}$Ga ions.

10. The conjugate, or pharmaceutically acceptable salt thereof, of any one of clause 8 to 9 wherein the metal ion is a gallium ion.

11. The conjugate, or pharmaceutically acceptable salt thereof, of any one of clauses 8 to 10 wherein the metal ion is a $^{66}$Ga ion.

12. The conjugate, or pharmaceutically acceptable salt thereof, of any one of clauses 8 to 10 wherein the metal ion is a $^{68}$Ga ion.

13. The conjugate, or pharmaceutically acceptable salt thereof, of any one of clauses 8 to 9 wherein the metal ion is a zirconium ion.

14. The conjugate, or pharmaceutically acceptable salt thereof, of clause 13 wherein the metal ion is an $^{89}$Zr ion.

15. The conjugate, or pharmaceutically acceptable salt thereof, of any one of clauses 8 to 9 wherein the metal ion is a copper ion.

16. The conjugate, or pharmaceutically acceptable salt thereof, of clause 15 wherein the metal ion is a $^{64}$Cu ion.

17. A composition comprising the conjugate, or a pharmaceutically acceptable salt thereof, of any one of clauses 1 to 16, and a pharmaceutically acceptable carrier therefor.

18. A kit comprising the conjugate, or a pharmaceutically acceptable salt thereof, of any one of clauses 1 to 17.

DETAILED DESCRIPTION OF ILLUSTRATIVE EMBODIMENTS

In accordance with the disclosure herein, the embodiments of the enumerated clauses provided in the Summary above, or any combination thereof, are contemplated for combination with any of the embodiments described in the Detailed Description section of this patent application.

In one illustrative and non-limiting embodiment described herein, conjugates and compositions described herein are used for diagnosing, imaging, and/or monitoring various diseases. In another embodiment, uses of conjugates and compositions are described herein for manufacturing medicaments for imaging, diagnosing, and/or monitoring various diseases. In another embodiment, uses of the conjugates and compositions described herein for imaging, diagnosing, and/or monitoring various diseases are provided. In another embodiment, kits are described herein for preparing and/or using the conjugates and compositions described herein for imaging, diagnosing, and/or monitoring various diseases.

The conjugates and compositions described herein are used to image, diagnose, and/or monitor various diseases, such as cancer. In one embodiment, the conjugates or compositions described herein can be used for both human clinical medicine and veterinary applications. Thus, a "patient" can be administered the conjugates or compositions described herein, and the patient can be human or, in the case of veterinary applications, can be a laboratory, agricultural, domestic, or wild animal. In one aspect, the patient can be a human, a laboratory animal such as a rodent (e.g., mice, rats, hamsters, etc.), a rabbit, a monkey, a chimpanzee, a domestic animal such as a dog or a cat, an agricultural animal such as a cow, a horse, a pig, a sheep, a goat, and a wild animal in captivity such as a bear, a panda, a lion, a tiger, a leopard, an elephant, a zebra, a giraffe, a gorilla, a dolphin, and a whale.

In various embodiments, the cancers described herein can be cancers that are tumorigenic, including benign tumors and malignant tumors, or the cancer can be non-tumorigenic. In another embodiment, the cancer can arise spontaneously or by such processes as mutations present in the germline of the patient or by somatic mutations, or the cancer can be chemically-, virally-, or radiation-induced. Exemplary cancers include, but are not limited to, a carcinoma, a sarcoma, a lymphoma, a melanoma, a mesothelioma, a nasopharyngeal carcinoma, a leukemia, an adenocarcinoma, and a myeloma.

In some aspects, the cancer can be lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, prostate cancer, leukemia, lymphoma, pleural mesothelioma, cancer of the bladder, Burkitt's lymphoma, cancer of the ureter, cancer of the kidney, neoplasms of the central nervous system, brain cancer, pituitary adenoma, or adenocarcinoma of the gastroesophageal junction.

In various embodiments, the conjugates used for imaging, diagnosing and/or monitoring diseases, such as cancer, can be a conjugate of the formula

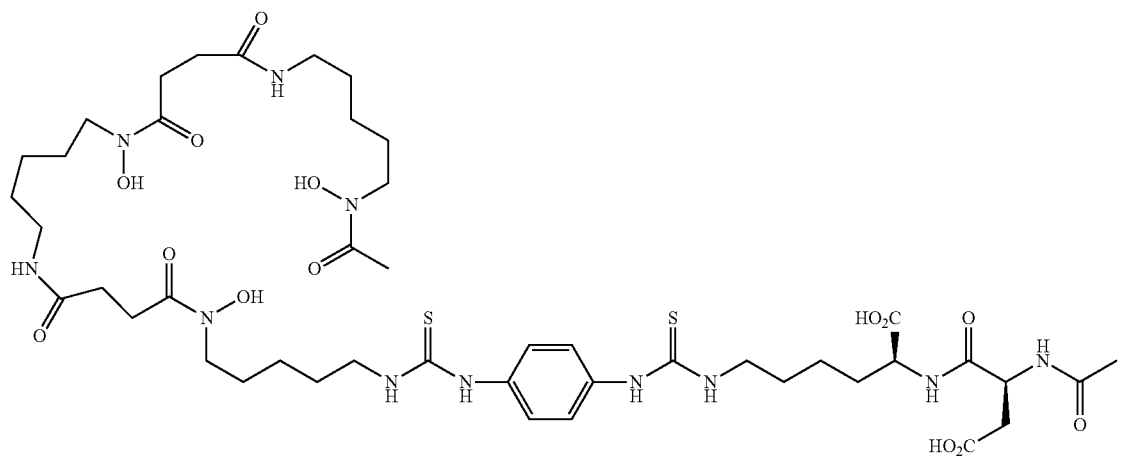

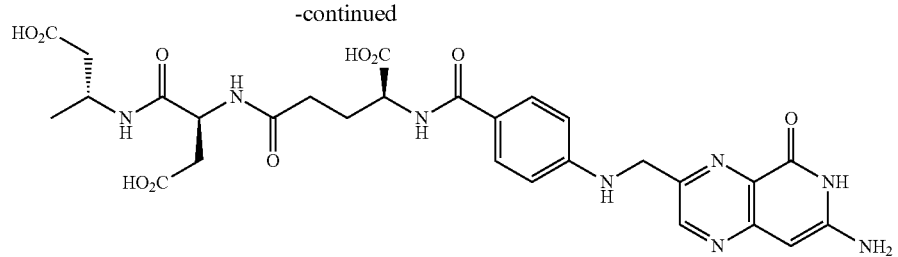
or a pharmaceutically acceptable salt thereof,
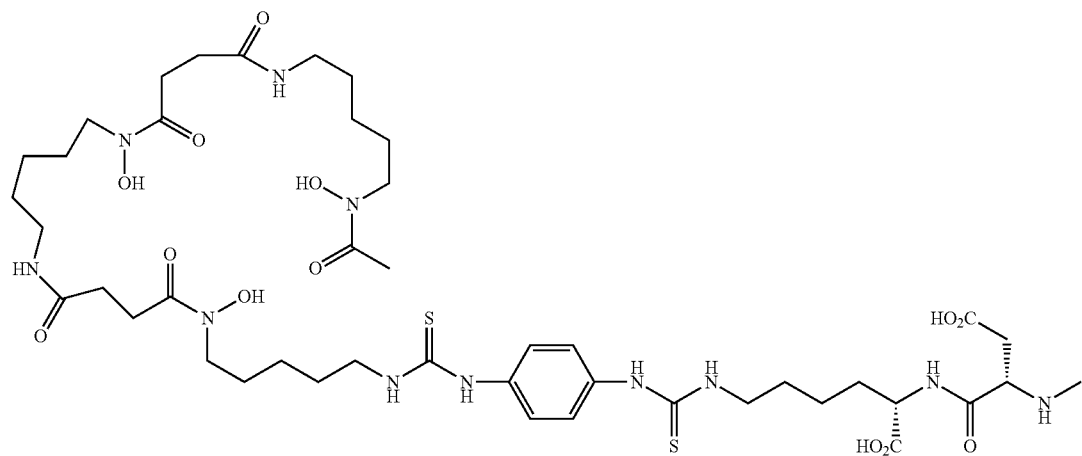
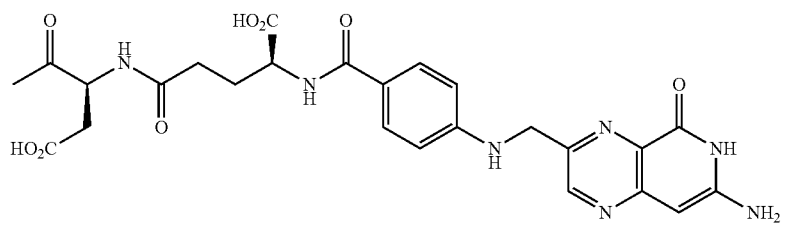
or a pharmaceutically acceptable salt thereof,
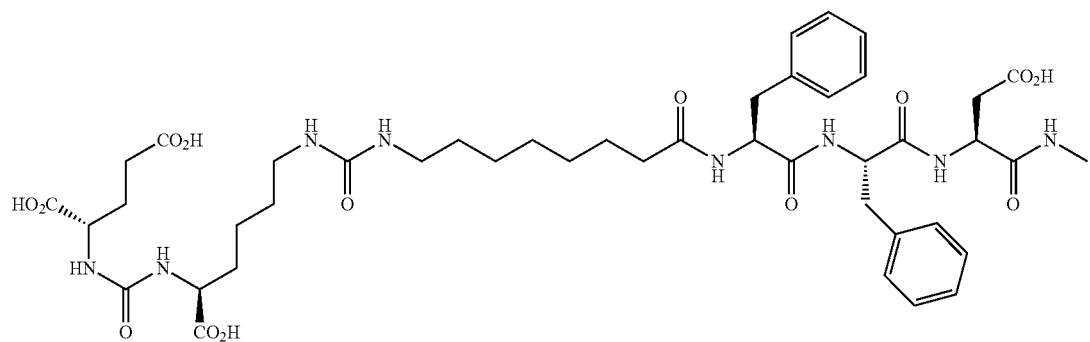

-continued
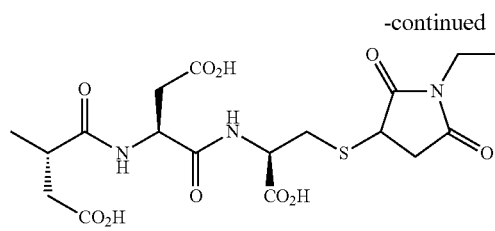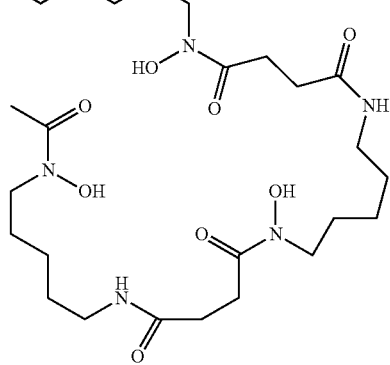
or a pharmaceutically acceptable salt thereof,
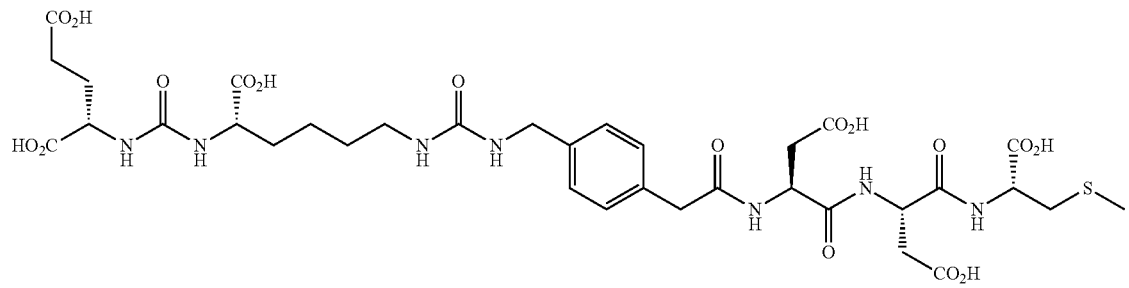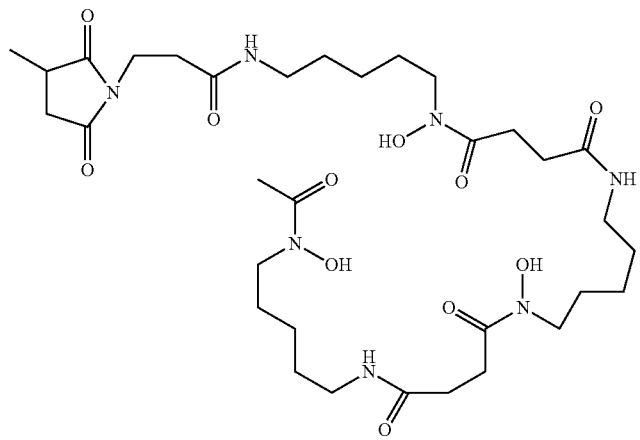
or a pharmaceutically acceptable salt thereof, or
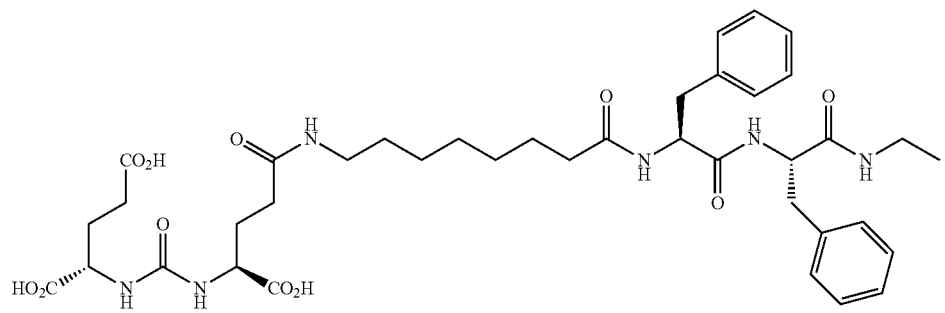

-continued

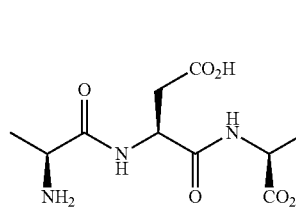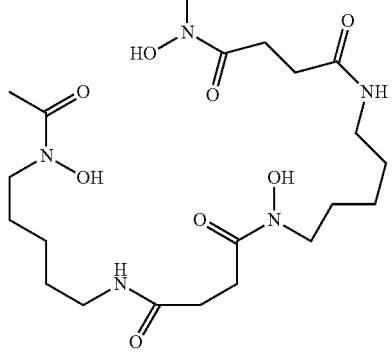

or a pharmaceutically acceptable salt thereof.

In each of the conjugate and composition embodiments described herein, the formulae may include not only all pharmaceutically acceptable salts of the conjugates, but also may include any and all hydrates and/or solvates of the conjugates. In another embodiment, certain functional groups, such as the hydroxy, amino, and like groups form complexes and/or coordination compounds with water and/or various solvents, in the various physical forms of the conjugates described herein. Accordingly, in some embodiments, the above formulae are to be understood to be a description of such hydrates and/or solvates, including pharmaceutically acceptable solvates.

In each of the foregoing and each of the following embodiments, the conjugates described herein may include each possible isomer, such as stereoisomers and geometric isomers, both individually and in any and all possible mixtures, of the formulae described herein. In each of the foregoing and each of the following embodiments, the conjugates may include any and all crystalline forms, partially crystalline forms, and non-crystalline and/or amorphous forms of the conjugates.

As used herein, the term "solvates" refers to conjugates described herein complexed with a solvent molecule. In one embodiment, the conjugates described herein may form such complexes with solvents by simply mixing the conjugates with a solvent, or dissolving the conjugates in a solvent. In the embodiment where the conjugates are to be used as pharmaceuticals, such solvents can be pharmaceutically acceptable solvents. In another embodiment, where the conjugates are to be used as pharmaceuticals, the relative amount of solvent that forms the solvate should be less than established guidelines for such pharmaceutical uses, such as less than International Conference on Harmonization (ICH) Guidelines. In yet another embodiment, the solvates may be isolated from excess solvent by evaporation, precipitation, and/or crystallization. In some embodiments, the solvates are amorphous, and in other embodiments, the solvates are crystalline.

In the conjugates described herein, the imaging moiety for producing, for example, a PET image may include one or more positron-emitting radionuclides, such as, but not limited to, radionuclides selected from the group consisting of $^{89}$Zr, $^{45}$Ti, $^{51}$Mn, $^{64}$Cu, $^{62}$CU, $^{61}$CU, $^{60}$Cu, $^{63}$Zn, $^{82}$Rb, $^{86}$Y, $^{68}$Ga, and $^{66}$Ga. In another embodiment, the radionuclide is a metal ion, such as a positron-emitting metal ion. In another embodiment, the radionuclide is a gallium ion, such as a positron-emitting gallium ion. In another embodiment, the radionuclide is selected from the group consisting of $^{89}$Zr, $^{64}$Cu, $^{68}$Ga, and $^{66}$Ga. In another illustrative embodiment, the radionuclide is selected from the group consisting of $^{89}$Zr, $^{64}$Cu, and $^{68}$Ga. In another embodiment, the radionuclide is $^{68}$Ga or $^{89}$Zr. In another embodiment in each of the foregoing and following embodiments described herein, the radionuclide is $^{68}$Ga. In another embodiment in each of the foregoing and following embodiments described herein, the radionuclide is $^{89}$Zr. In another embodiment in each of the foregoing and following embodiments described herein, the radionuclide is $^{64}$Cu. In one aspect, factors that may influence selection of a suitable radionuclide include sufficient half-life of the positron-emitting radionuclide to permit preparation of a diagnostic composition in a pharmaceutically acceptable carrier prior to administration to the patient, and sufficient remaining half-life to yield sufficient activity to permit extra-corporeal imaging by a PET scan. In yet another aspect, a suitable radionuclide should have a sufficiently short half-life to limit patient exposure to unnecessary radiation.

Illustrative positron-decaying radionuclides having suitable half-lives include $^{45}$Ti, half-life about 3 hours; $^{61}$Cu, half-life about 3.4 hours; $^{63}$Zn, half-life about 38 minutes; $^{82}$Rb, half-life about 2 minutes; $^{68}$Ga, half-life about 68 minutes, $^{66}$Ga, half-life about 9.5 hours; and $^{89}$Zr, half-life about 78.4 hours.

In other embodiments, pharmaceutically acceptable salts of the conjugates are described. In one aspect, pharmaceutically acceptable salts of the conjugates described herein include acid addition and base salts thereof. Suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts of the conjugates described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In one embodiment, the conjugates described herein may be administered as a formulation in association with one or more pharmaceutically acceptable carriers. In one illustrative aspect, the carriers can be excipients. In one embodiment, the choice of carrier will to a large extent depend on factors such as the particular mode of administration, the effect of the carrier on solubility and stability, and the nature of the dosage form. In one illustrative aspect, pharmaceutically acceptable carriers for the delivery of the conjugates described herein and methods for their preparation will be readily apparent to those skilled in the art. Such compositions and methods for their preparation may be found, for example, in Remington: The Science & Practice of Pharmacy, 21th Edition (Lippincott Williams & Wilkins, 2005), incorporated herein by reference. In some embodiments, the carrier is suitable for parenteral administration and can be in a sterile aqueous solution.

In one embodiment, a kit is described comprising any of the conjugates, or a pharmaceutically acceptable salt thereof, described herein. In one aspect, such a kit can comprise one or more separate pharmaceutical compositions, at least one of which contains a conjugate, or a pharmaceutically acceptable salt thereof, as described herein. In another embodiment, the kit can comprise a conjugate, or a pharmaceutically acceptable salt thereof, as described herein and one or more separate compositions for labeling the conjugate, or pharmaceutically acceptable salt thereof, with, for example, a metal ion. In another embodiment, means for separately retaining the compositions, such as a container, divided bottle, or divided foil packet are included in the kit. In another embodiment, compositions comprising one or more conjugates described herein, in containers having labels that provide instructions for use of the conjugates are described. In another embodiment, the compositions in the kit are in the form of reconstitutable lyophilizates. In another embodiment, the compositions are in liquid form. In yet another embodiment, the compositions are each in a sterile vial or container.

The following examples further illustrate specific embodiments of the invention; however, the following illustrative examples should not be interpreted in any way to limit the invention.

CONJUGATE EXAMPLES

Procedures for Synthesis of Pet Imaging Agents

Synthesis of EC2418:

TABLE

Reagents for peptide synthesis

| Reagents | mmol | equivalent | MW (g/mol) | Amount |
|---|---|---|---|---|
| Fmoc-Lys(MTT)-Resin (0.38 mmol/g) | 1.0 | | | 2.632 g |
| Fmoc-Asp(Ot-Bu)-OH | 2.0 | 2 | 411.5 | 0.822 g |
| Fmoc-Asp(Ot-Bu)-OH | 2.0 | 2 | 411.5 | 0.822 g |
| Fmoc-Glu-Ot-Bu | 2.0 | 2 | 425.5 | 0.850 g |
| $N^{10}$TFA-Pteroic Acid (dissolve in 10 ml DMSO) | 1.5 | 1.5 | 408 | 0.612 g |
| DIPEA | 4.0 | 4 | 129.25 (d = 0.742) | 0.697 mL |
| PyBOP | 2.0 | 2 | 520 | 1.040 g |

Coupling Steps:

Initial Peptide Synthesis on-Resin:

Commercially available 100-200 mesh peptide-loaded resin was utilized in an AAPPTec-sourced peptide synthesizer equipped with DMF, DMF-Peptide, DMF-PyBOP, DMF-DIPEA, and DMF-piperidine solutions. The desired peptide sequence was programmed into the software interface and run in an automated fashion. Upon completion of the sequence, the peptide-loaded resin was removed from the instrument's reaction flask. Analysis of the resin-peptide was conducted by taking a small quantity of beads, cleaving with TFA and analyzing the filtered solution by LCMS (1-50% ACN/10 mM NH4OAc, pH 5).

Cleavage of Peptide from Resin and Purification:

Peptide was cleaved from the loaded resin by a mixture of 95% TFA, 2.5% TIPS, 2.5% $H_2O$. Resin was subjected to cleavage mixture under Argon for 35 min, drained, followed by treatment with fresh cleavage mixture for 5 min and drained (2×). The combined peptide-TFA solution was diluted with ether to precipitate the peptide and collected by centrifuge. Peptide cake was washed with ether and dried. Crude peptide was suspended in water and $Na_2CO_3$ was added and maintained at pH 9-10 for 1 h. The reactions mixture was acidified with 1N HCl to pH 4.0 and purified using a Biotage reverse-phase C18 column (Mobile phase A=0.1% TFA buffer and B=ACN). Product fractions were collected, combined, acetonitrile was removed and the resulting solution freeze-dried to yield EC2418 (496 mg, 62%). LCMS (ESI): [M+H]$^+$=Calculated for $C_{33}H_{41}N_{11}O_{13}$, 800.29; found 800.36.

Synthesis of EC2419:

EC2418

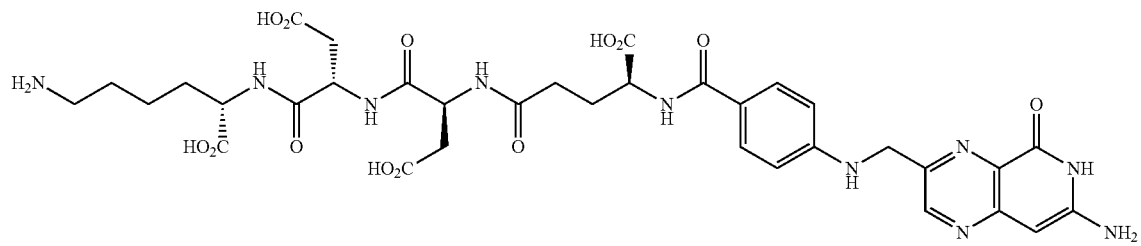

Chemical Formula: $C_{33}H_{41}N_{11}O_{13}$
Exact Mass: 799.29
Molecular Weight: 799.74

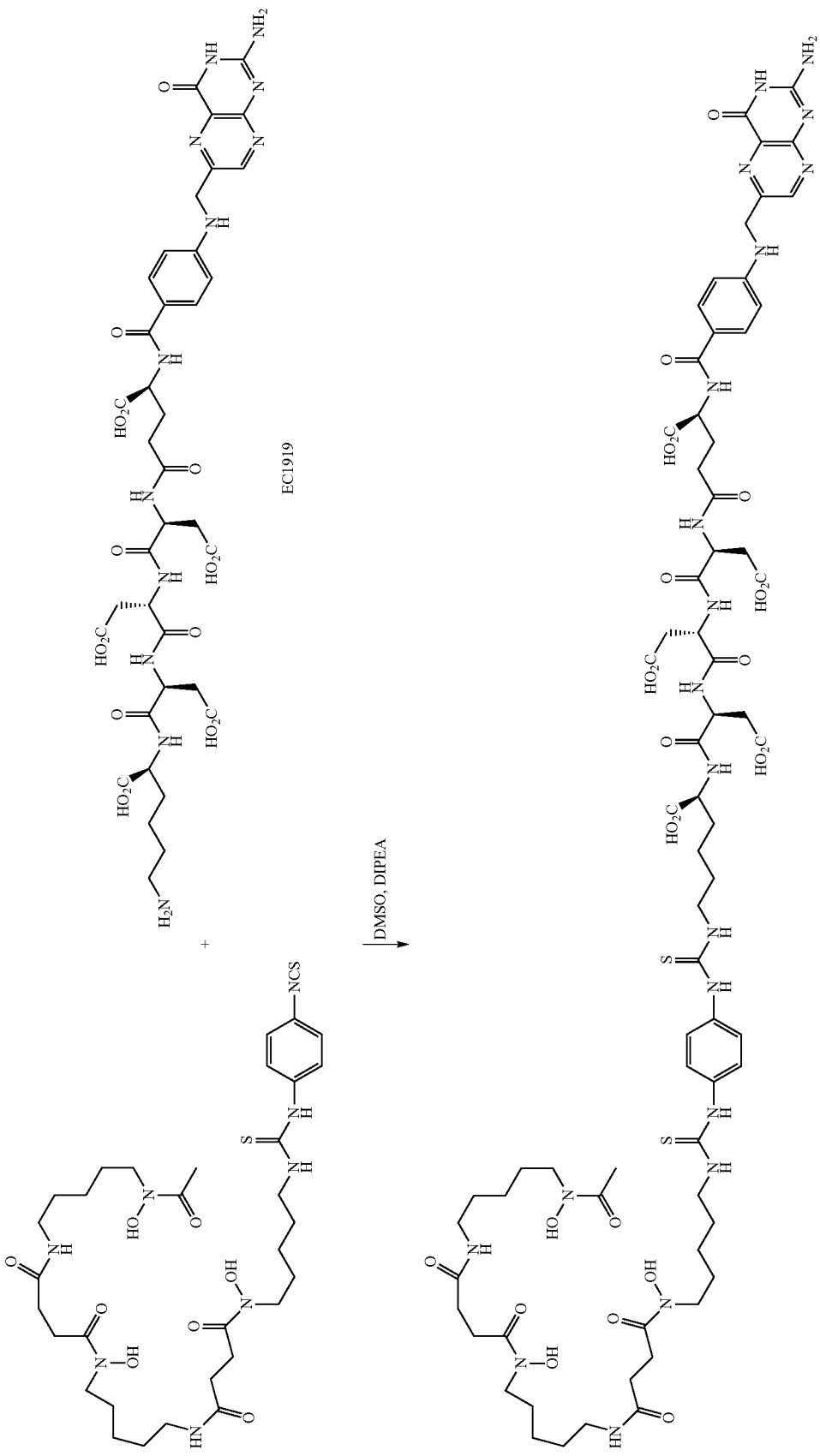

To a solution of EC1919 (213 mg, 0.23 mM) in DMSO (3.0 mL) and DIPEA (0.88 mL) was added P-SCN-Bn-Deferoxamine (175 mg, 0.23 mM) in DMSO (4.0 mL). The solution was stirred at ambient temperature under argon for 3 h. Reaction mixture was loaded directly onto a Biotage column (mobile phase A=50 mM ammonium bicarbonate buffer, pH=7.0. B=ACN) for purification. Fractions containing the desired product were collected, combined, acetonitrile was removed and the resulting solution freeze-dried to afford the EC2419 (308 mg, 80.3%) as a light yellow solid. LCMS (ESI): [M+H]$^+$=Calculated for $C_{70}H_{98}N_{20}O_{24}S_2$, 1667.65; found 1667.79.

Synthesis of EC2420:

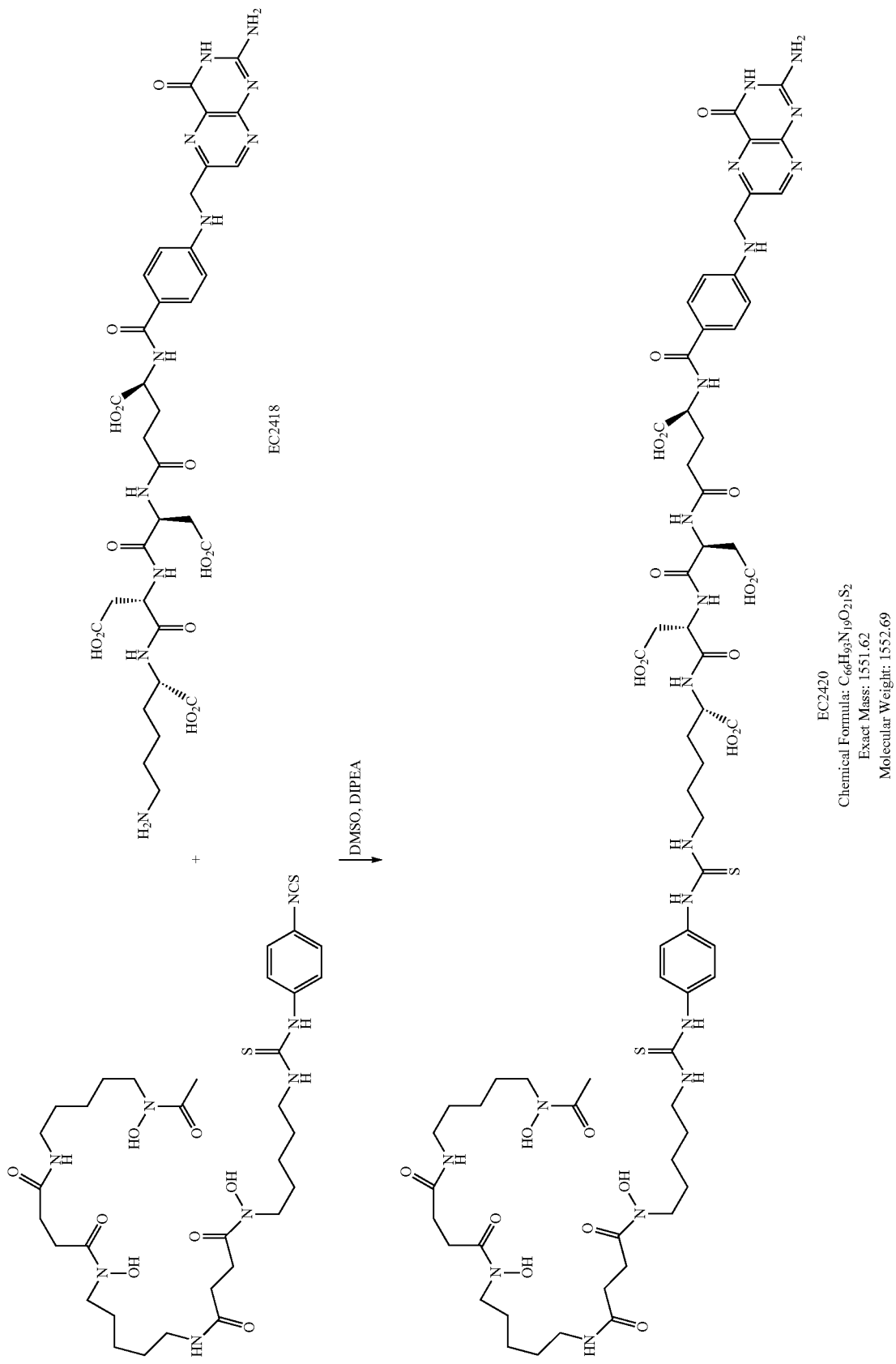

To a solution of EC2418 (133.9 mg, 0.167 mM) in DMSO (1.0 mL) and DIPEA (0.58 mL) was added P-SCN-Bn-deferoxamine (105 mg, 0.14 mM) in DMSO (3.0 mL) and stirred at ambient temperature under argon for 3 h. Reaction mixture was loaded directly onto a Biotage column (mobile phase A=50 mM ammonium bicarbonate buffer, pH=7.0. B=ACN) for purification. Fractions containing the desired product were collected, combined, acetonitrile was removed and the resulting solution freeze-dried to afford the EC2420 (165 mg, 75.9%) as a light yellow solid. LCMS (ESI): $[M+H]^+$=Calculated for $C_{66}H_{93}N_{19}O_{21}S_2$, 1552.62; found 1552.71.

Synthesis of EC2448:

removed from the instrument's reaction flask. Analysis of the resin-peptide was conducted by taking a small quantity of beads, cleaving with TFA and analyzing the filtered solution by LCMS (1-50% ACN/10 mM $NH_4OAc$, pH5).

Addition of Ec1380 to Resin-Bound Peptide:

Resin-bound Peptide obtained through automated synthesis was placed in a traditional bench top solid-phase reaction vessel. N-Fmoc protection was removed using 20% piperidine in DMF under argon for 10 minutes (3×). The resin was then rinsed with DMF (3×), and IPA (3×). The removal of Fmoc was confirmed by Kaiser Test. The resin was then rinsed with DMF (3×) and suspended in DMF, with the addition of 2eq of EC1380, 2eq of PyBOP, and 4eq of

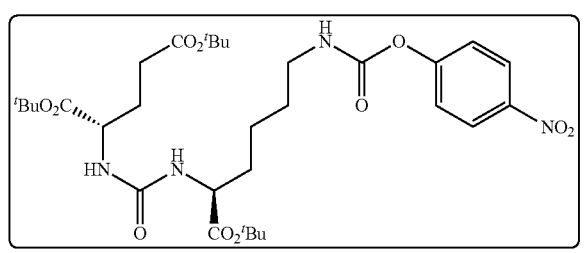

EC1380

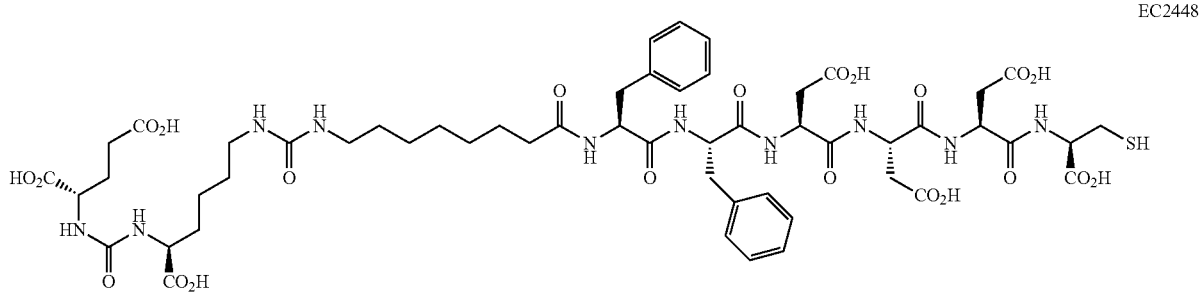

EC2448

Chemical Formula: C54H74N10O22S
Exact Mass: 1246.47
Molecular Weight: 1247.28

TABLE

Reagents for peptide synthesis

| Reagents | mmol | equivalent | MW (g/mol) | Amount |
|---|---|---|---|---|
| Fmoc-Cys(trt)-Resin (0.60 mmol/g) | 0.5 | | | 0.833 g |
| Fmoc-Asp(Ot-Bu)-OH | 1.0 | 2 | 411.5 | 0.411 g |
| Fmoc-Asp(Ot-Bu)-OH | 1.0 | 2 | 411.5 | 0.411 g |
| Fmoc-Asp(Ot-Bu)-OH | 1.0 | 2 | 411.5 | 0.411 g |
| Fmoc-Phe-OH | 1.0 | 2 | 387.4 | 0.387 g |
| Fmoc-Phe-OH | 1.0 | 2 | 387.4 | 0.387 g |
| Fmoc-8-aminocaprylic Acid | 1.0 | 2 | 381.4 | 0.381 g |
| EC1380 | 1.0 | 2 | 652.7 | 0.653 g |
| DIPEA | 2.0 | 4 | 129.25 (d = 0.742) | 0.348 mL |
| PyBOP | 1.0 | 2 | 520 | 0.520 g |

Coupling Steps:
Initial Peptide Synthesis on-Resin:

Commercially-available 100-200 mesh peptide-loaded resin was utilized in an AAPPTec-sourced peptide synthesizer equipped with DMF, DMF-Peptide, DMF-PyBOP, DMF-DIPEA, and DMF-piperidine solutions. The desired peptide sequence, except EC1380, was programmed into the software interface and run in an automated fashion. Upon completion of the sequence, the peptide-loaded resin was DIPEA. After 1-2 h of argon bubbling, the solvent was drained and the resin rinsed with DMF (3×), and IPA (3×). Analysis of the resin-peptide was conducted by taking a small quantity of beads, cleaving with TFA and analyzing the filtered solution by LCMS (1-50% ACN/10 mM $NH_4OAc$, pH5).

Cleavage of Peptide from Resin and Purification:

Peptide was cleaved from the loaded resin by a mixture of 92.5% TFA, 2.5% TIPS, 2.5% $H_2O$, and 2.5% EDT. Resin was subjected to cleavage mixture under Argon for 35 min, drained, followed by treatment with fresh cleavage mixture for 5 min and drained (2×). The resulting peptide-TFA solution was diluted with ether to precipitate the peptide and collected by centrifuge. Peptide cake was washed with ether and dried. Crude peptide was purified using a Biotage reverse-phase C18 column (Mobile phase A=0.1% TFA buffer and B=ACN). Product fractions were collected, combined, acetonitrile was removed and freeze-dried to yield EC2448 (240 mg, 38.5%) LCMS (ESI): $[M+H]^+$=Calculated for $C_{54}H_{74}N_{10}O_{22}S$, 1247.47; found 1247.51.

Synthesis of EC2450:

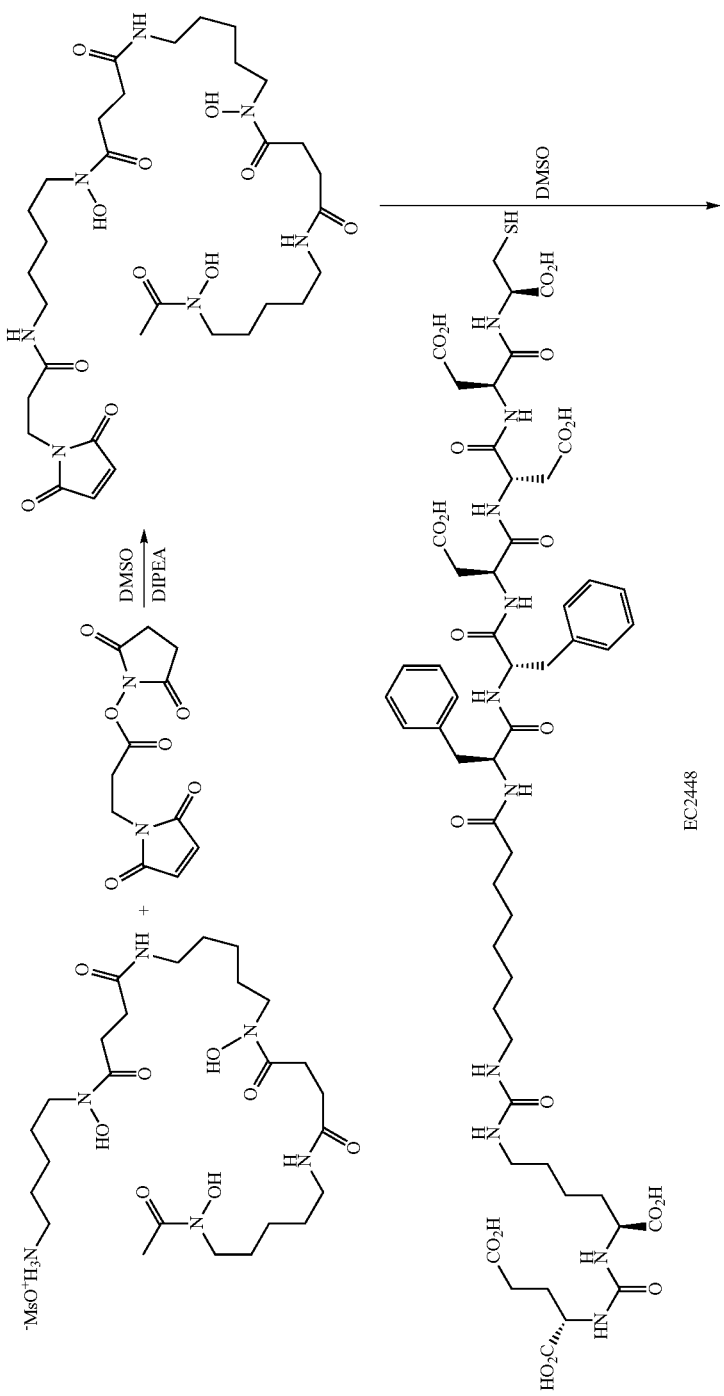

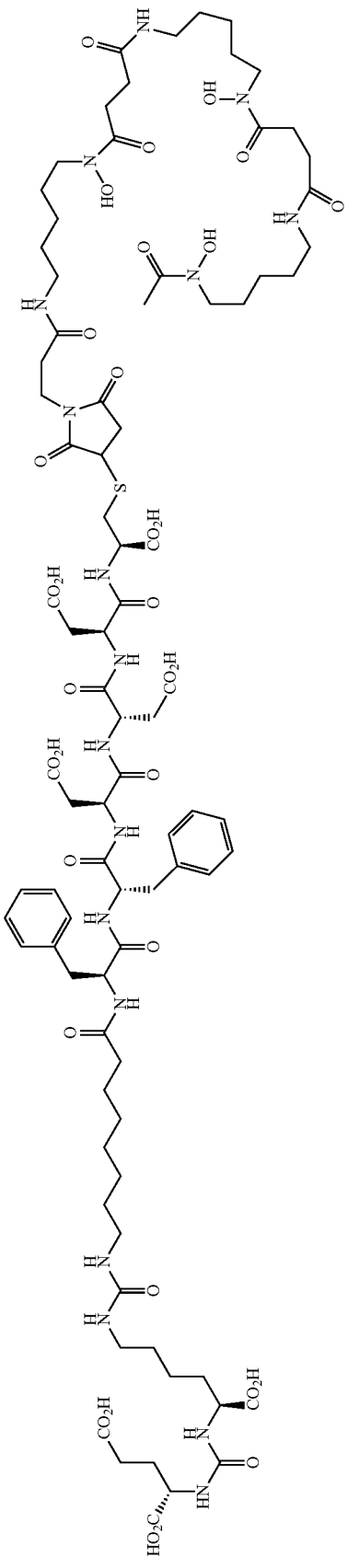
EC2450
Chemical Formula: $C_{86}H_{127}N_{17}O_{33}S$
Exact Mass: 1957.85
Molecular Weight: 1959.09

To a solution of deferoxamine mesylate (65.7 mg, 0.1 mM) in DMSO (0.3 mL) and DIPEA (0.087 mL) was added β-maleimido-propionic acid N-hydroxysuccinimide ester (26.6 mg, 0.1 mM) in DMSO (0.3 mL) and stirred at ambient temperature under argon for 1 h. Solution of EC2448 (118.5 mg, 0.095 mM) in DMSO (0.5 mL) and DIPEA (0.26 mL) were added and stirred for additional 30 min. Reaction mixture was loaded directly onto a Biotage column (mobile phase A=50 mM ammonium bicarbonate buffer, pH=7.0. B=ACN) for purification. Fractions containing the desired product were collected, combined, acetonitrile was removed and freeze-dried to afford the EC2450 (56 mg, 30.1%, over two steps) as a white solid. LCMS (ESI): $[M-2H]^{2-}$=Calculated for $C_{86}H_{127}N_{17}O_{33}S$, 978.54; found 978.55.

Synthesis of EC2458:

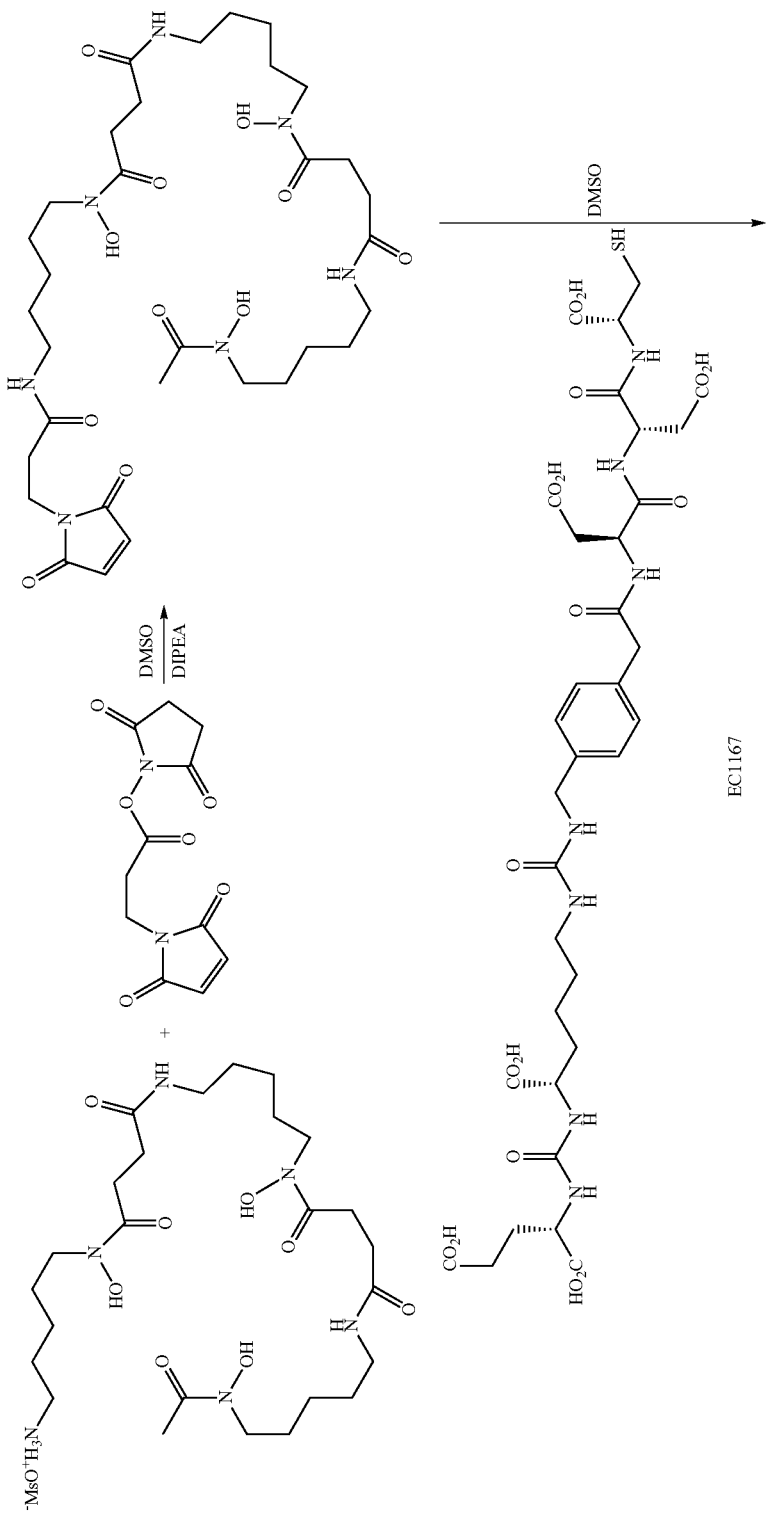

-continued
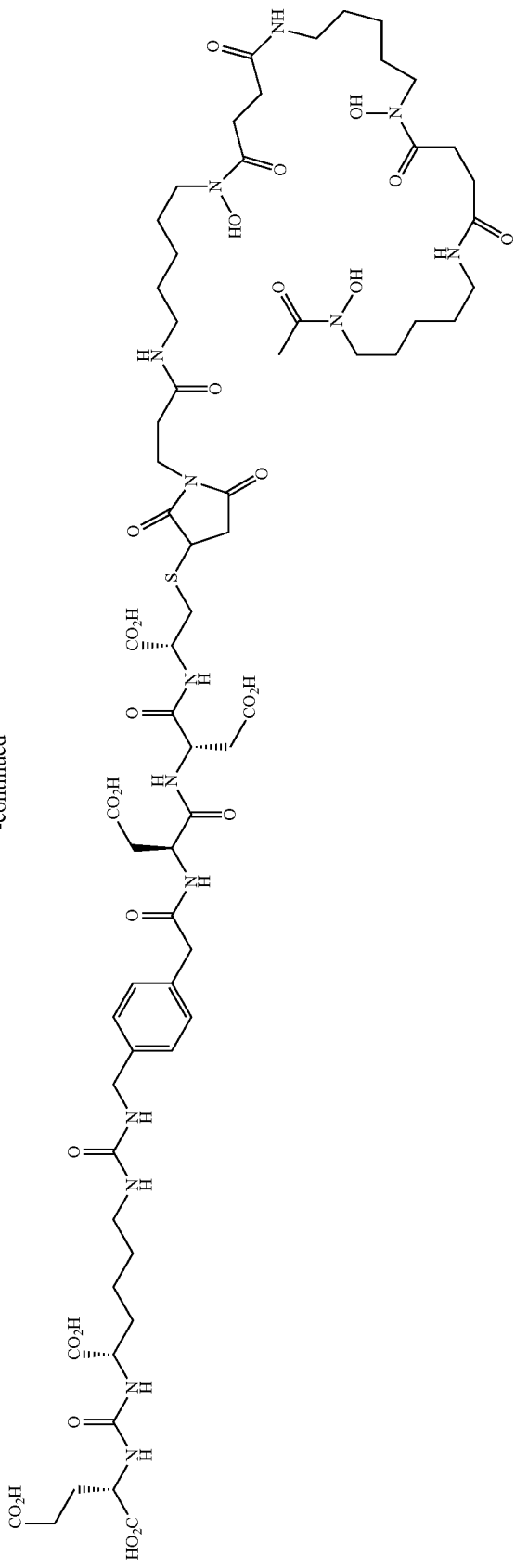
EC2458
Chemical Formula: $C_{65}H_{98}N_{14}O_{28}S$
Exact Mass: 1554.64
Molecular Weight: 1555.62

To a solution of deferoxamine mesylate (65.7 mg, 0.1 mM) in DMSO (0.3 mL) and DIPEA (0.087 mL) was added β-maleimido-propionic acid N-hydroxysuccinimide ester (26.6 mg, 0.1 mM) in DMSO (0.3 mL) and stirred at ambient temperature under argon for 1 h. Solution of EC1167 (92.8 mg, 0.11 mM) in DMSO (1.0 mL) was added and stirred for additional 3 h. Reaction mixture was loaded directly onto a Biotage column (mobile phase A=50 mM ammonium bicarbonate buffer, pH=7.0. B=ACN) for purification. Fractions containing the desired product were collected, combined, acetonitrile was removed and the resulting solution freeze-dried to afford the EC2458 as a white solid. LCMS (ESI): [M−2H]$^{2-}$=Calculated for $C_{65}H_{98}N_{14}O_{28}S$, 776.81; found 776.67.

Synthesis of EC2460:

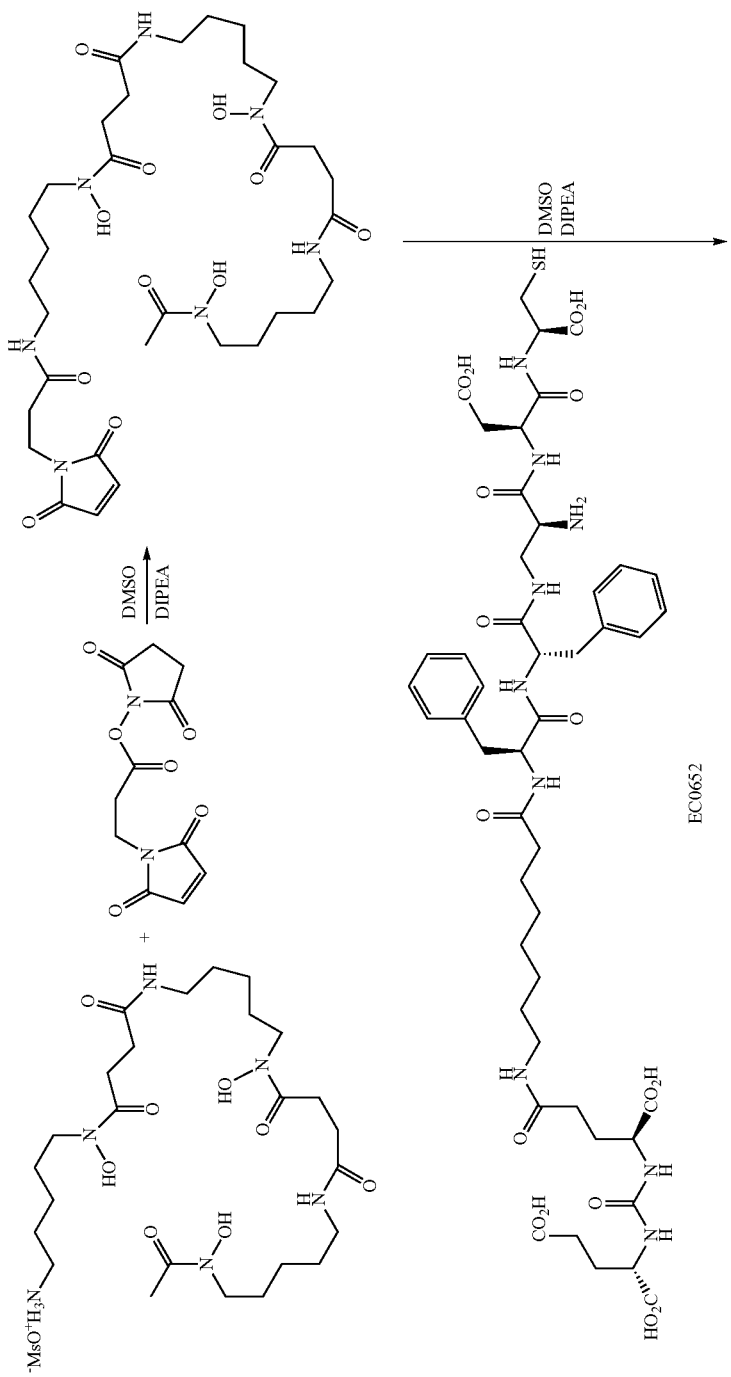

-continued
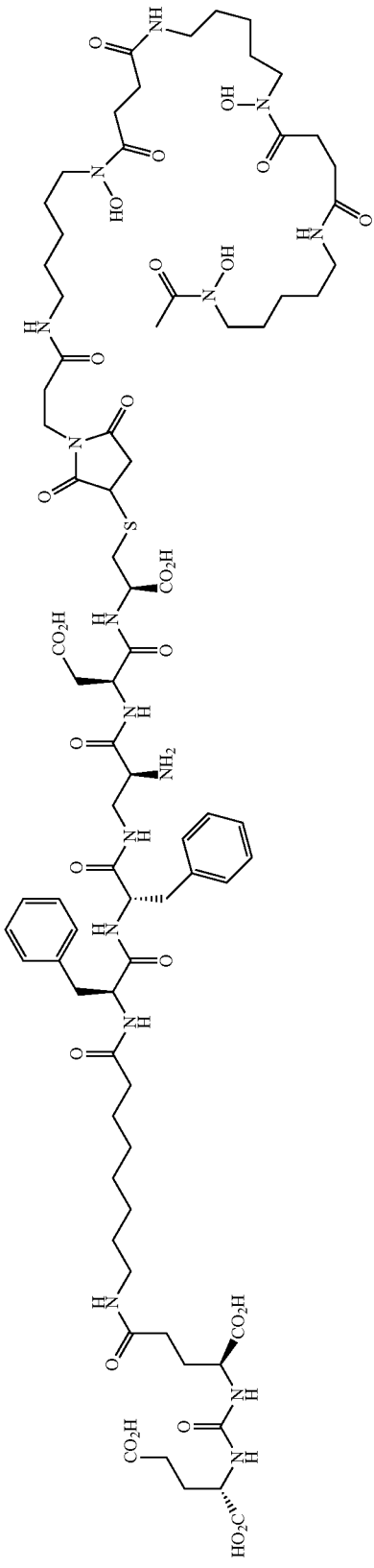
EC2460
Chemical Formula: $C_{79}H_{118}N_{16}O_{28}S$
Exact Mass: 1770.80
Molecular Weight: 1771.94

To a solution of deferoxamine mesylate (65.7 mg, 0.1 mM) in DMSO (0.3 mL) and DIPEA (0.087 mL) was added β-maleimido-propionic acid N-hydroxysuccinimide ester (26.6 mg, 0.1 mM) in DMSO (0.3 mL) and stirred at ambient temperature under argon for 1 h. Solution of EC0652 (116.6 mg, 0.11 mM) in DMSO (0.5 mL) was added and stirred for additional 30 min. Reaction mixture was loaded directly onto a Biotage column (mobile phase A=50 mM ammonium bicarbonate buffer, pH=7.0. B=ACN) for purification. Fractions containing the desired product were collected, combined, acetonitrile was removed and the resulting solution freeze-dried to afford the EC2460 (116 mg, 65.4%, over two steps) as a white solid. LCMS (ESI): [M−2H]$^{2-}$ Calculated for $C_{79}H_{118}N_{16}O_{28}S$, 884.97; found 884.86.

The deferoxamine conjugates described above may be complexed to a positron emitting metal ion by any of the procedures known to those skilled in the art of producing PET-imaging conjugates and/or compounds.

What is claimed is:

1. A conjugate, or a pharmaceutically acceptable salt thereof, of the formula

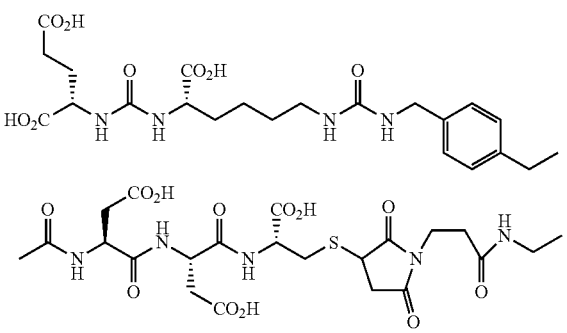

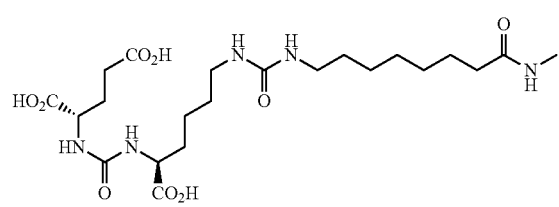

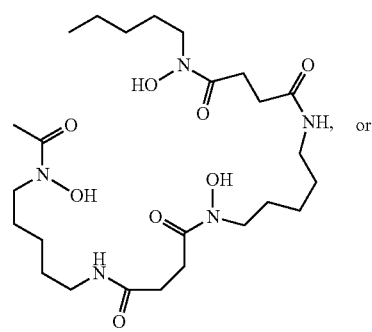

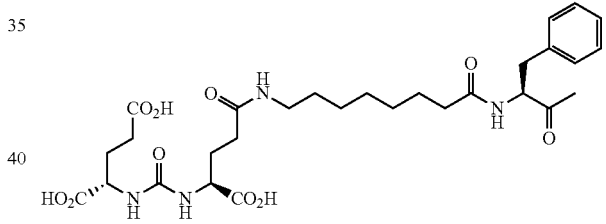

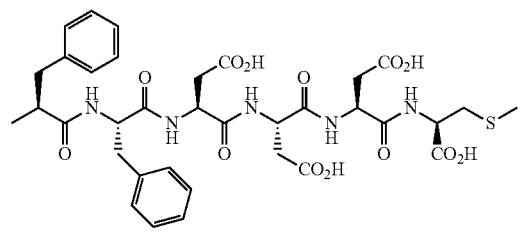

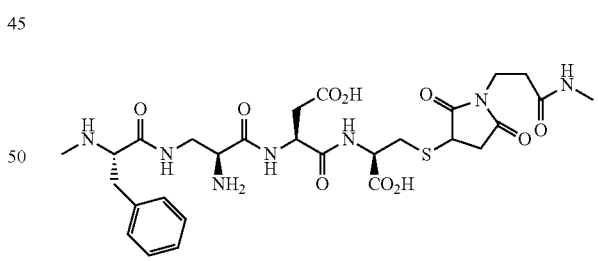

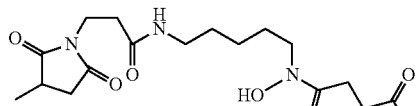

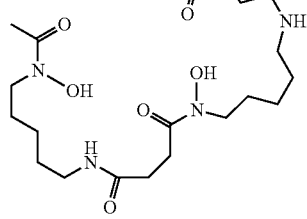

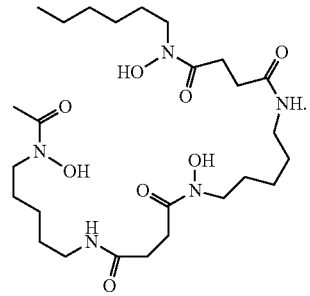

2. The conjugate of claim 1 of the formula
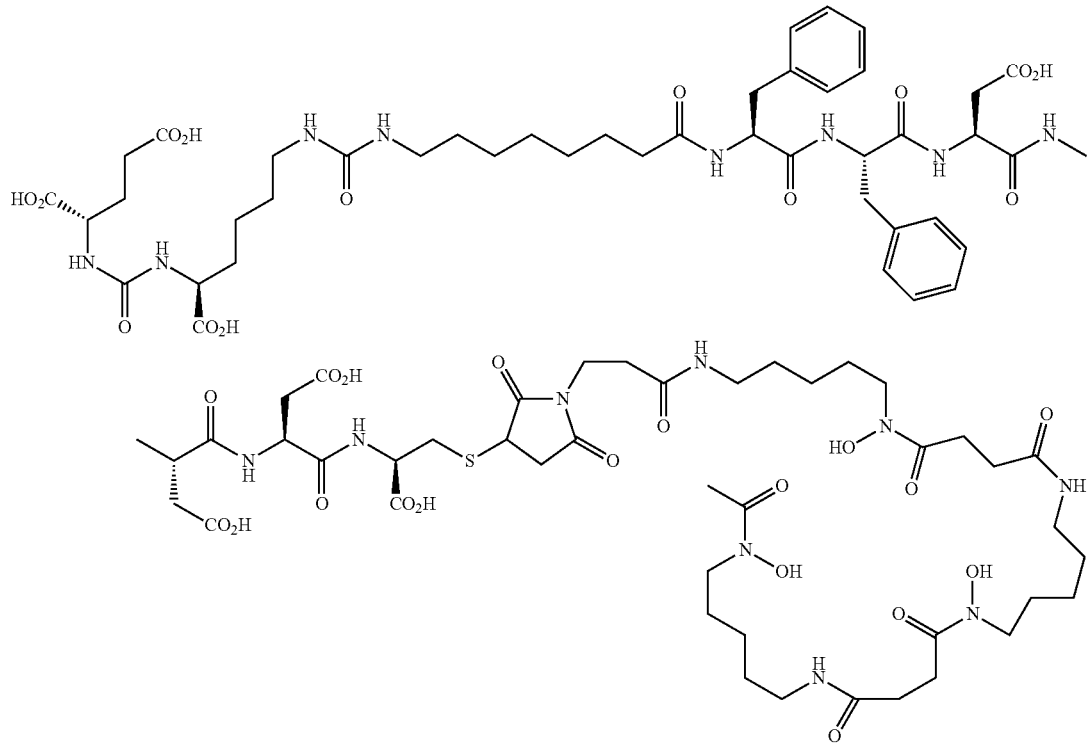
or a pharmaceutically acceptable salt thereof.
3. The conjugate of claim 1 of the formula
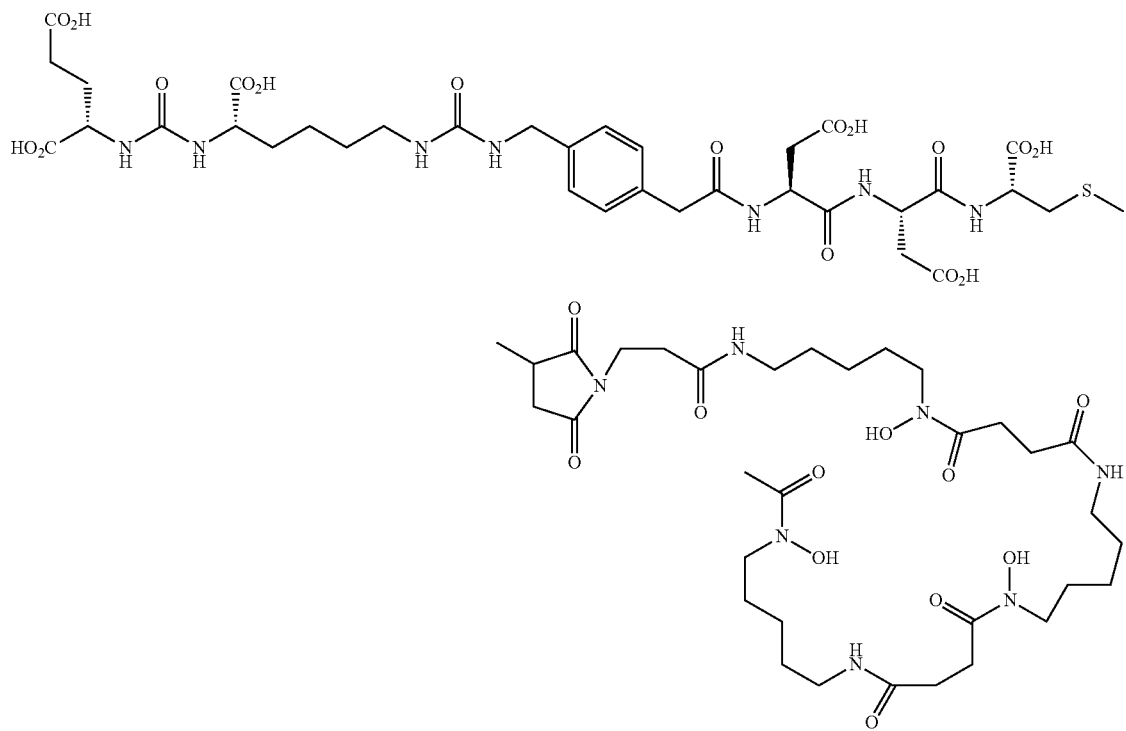
or a pharmaceutically acceptable salt thereof.

4. The conjugate of claim 1 of the formula

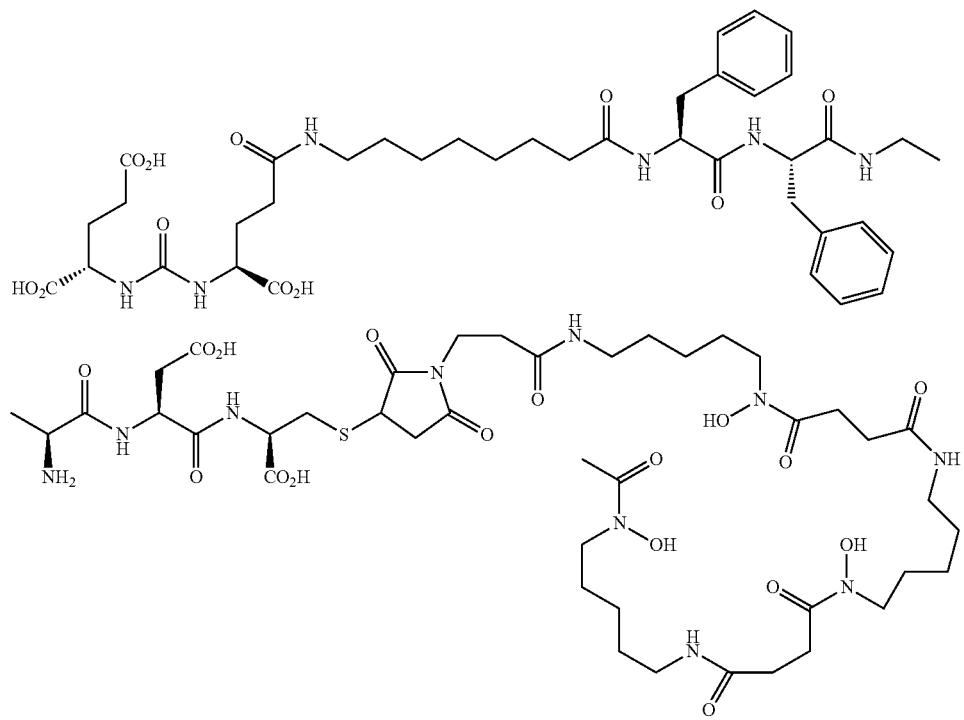

or a pharmaceutically acceptable salt thereof.

5. The conjugate of claim 1 wherein the conjugate, or pharmaceutically acceptable salt thereof, is complexed with $^{89}$Zr.

6. A composition comprising a conjugate, or a pharmaceutically acceptable salt thereof, of claim 1.

7. A kit comprising a conjugate, or a pharmaceutically acceptable salt thereof, of claim 1.

* * * * *